US012662462B2

(12) United States Patent
Jin et al.

(10) Patent No.: US 12,662,462 B2
(45) Date of Patent: Jun. 23, 2026

(54) SALTS OF PYRIDINYLMETHYLENEPIPERIDINE DERIVATIVES AND USES THEREOF

(71) Applicant: SUNSHINE LAKE PHARMA CO., LTD., Dongguan (CN)

(72) Inventors: Chuanfei Jin, Dongguan (CN); Wenhe Zhong, Dongguan (CN); Tengfei Xu, Dongguan (CN)

(73) Assignee: SUNSHINE LAKE PHARMA CO., LTD., Dongguan (CN)

( * ) Notice: Subject to any disclaimer, the term of this patent is extended or adjusted under 35 U.S.C. 154(b) by 423 days.

(21) Appl. No.: 18/270,351

(22) PCT Filed: Dec. 28, 2021

(86) PCT No.: PCT/CN2021/141955
§ 371 (c)(1),
(2) Date: Jun. 29, 2023

(87) PCT Pub. No.: WO2022/143622
PCT Pub. Date: Jul. 7, 2022

(65) Prior Publication Data

US 2024/0083870 A1 Mar. 14, 2024

(30) Foreign Application Priority Data

Dec. 29, 2020 (CN) ........................ 202011591371.3

(51) Int. Cl.
*C07D 401/06* (2006.01)
*C07C 309/04* (2006.01)

(52) U.S. Cl.
CPC .......... *C07D 401/06* (2013.01); *C07C 309/04* (2013.01); *C07B 2200/13* (2013.01)

(58) Field of Classification Search
CPC .. C07D 401/06; C07B 2200/13; C07C 309/04
See application file for complete search history.

(56) References Cited

U.S. PATENT DOCUMENTS

2021/0188803 A1* 6/2021 Jin .......................... A61P 25/24

OTHER PUBLICATIONS

Jin et al.; "Design, synthesis and biological evaluation of pyridinylmethylenepiperidine derivatives as potent 5-HT1F receptor agonists for migraine therapy;" European Journal of Medicinal Chemistry; 2021; pp. 1-12; vol. 225, No. 113782.

Mar. 28, 2022 Search Report issued in International Patent Application No. PCT/CN2021/141955.

Mar. 28, 2022 Written Opinion of the International Searching Authority issued in International Patent Application No. PCT/CN2021/141955.

* cited by examiner

*Primary Examiner* — Timothy R Rozof
(74) *Attorney, Agent, or Firm* — Oliff PLC

(57) ABSTRACT

Salts of pyridinylmethylenepiperidine derivatives and uses thereof including pharmaceutical composition including the salts, and uses of the salts and the pharmaceutical composition including the salts in the manufacture of a medicament for preventing, treating or lessening diseases related to 5-$HT_{1F}$ receptors, especially migraine in a patient.

9 Claims, 11 Drawing Sheets

SALTS OF PYRIDINYLMETHYLENEPIPERIDINE DERIVATIVES AND USES THEREOF

CROSS-REFERENCE TO RELATED APPLICATION

This is a U.S. national stage application of the International Patent Application No. PCT/CN2021/141955, filed 28 Dec. 2021, which claims the priority and benefits of Chinese Patent Application No. 202011591371.3, filed with the State Intellectual Property Office of China on Dec. 29, 2020, both of which are incorporated herein by reference in their entireties.

FIELD

The present invention belongs to the technical field of medicine, and relates to salts of pyridinylmethylenepiperidine derivatives and uses thereof, in particular to salts of 2,4,6-trifluoro-N-(6-(fluoro(1-methylpiperidin-4-ylidene) methyl)pyridin-2-yl)benzamide, crystal forms of the salts and uses thereof, and further relates to a pharmaceutical composition comprising the salts or the crystal forms of the salts.

BACKGROUND

Migraine is a type of episodic and often unilateral pulsating headache, often accompanied by nausea and vomiting. It is a common chronic neurovascular disease. It often starts in children and adolescence, and reaches the peak of the disease in the young and middle-aged. It is more common in women, the ratio of male to female patients is about 1:2-3, and the prevalence rate in the population is 5%-10%, often with genetic background.

Although migraine is not a fatal disease, it can seriously affect the social life of patients. In the United States, the socio-economic burden caused by migraine is US$1-1.7 billion. In our country, there are also a large number of patients with migraine that affect their work, study and life. As the pace of life accelerates, the incidence of migraine is gradually increasing. A recent survey found that about 5.7% of men and 17.6% of women have an average of more than one migraine attack per year. In addition, there are still many people with a genetic predisposition to migraine.

The pathogenesis of migraine is complex and diverse, mainly including vascular origin theory, neurogenic theory, trigeminal neurovascular theory, biochemical factors and genetic factors. At present, the drugs used to treat migraine are mainly 5-HT$_{1B/D}$ receptor agonists triptans. However, because triptans can constrict blood vessels, they are contraindicated for patients with cardiovascular, cerebrovascular and peripheral vascular diseases. In addition, 40% to 70% of migraine patients have poor efficacy on triptans therapy, and ⅓ of patients with effective initial treatment often encounter headache recurrence. The efficacy of triptans on patients with moderate to severe headaches is significantly reduced. In order to overcome these adverse effects of triptans, anti-migraine drugs such as calcitonin gene-related peptide (CGRP) receptor antagonists and selective 5-HT$_{1F}$ receptor agonists have emerged. However, CGRP receptor antagonists still have many shortcomings. For example, olcagepant can only be used intravenously rather than taken orally. Long-term use of telcagepant can cause increased liver enzymes, and BI-44370 has been suspended clinical development due to its interaction with cytochrome P450. Therefore, there is an urgent need to develop new acute-phase therapeutic drugs. The development of selective 5-HT$_{1F}$ receptor agonists anti-migraine drugs has always been considered a new and promising approach.

Since 1938, the work of Graham and Wolff (Arch. Neurol. Psychiatry, 39: 737-63, 1938) has been dominant in theories about the pathophysiology of migraine. They proposed that the cause of migraine is vasodilation of extracranial blood vessels. This view is supported by the following evidence: Ergot alkaloids and sumatriptan, as a water-absorbing 5-HT$_1$ agonist that cannot cross the blood-brain barrier, can contract the smooth muscles of blood vessels in the head, and can effectively treat migraine (Humphrey, et al., Ann. NY Acad. Sci., 600: 587-600, 1990). However, the work of Moskowitz's research team has shown that migraine has nothing to do with changes in blood vessel diameter (Cephalalgia, 12: 5-7, 1992).

The Moskowitz's research team proposed that a currently unknown pain trigger stimulates the trigeminal ganglion (the trigeminal ganglion innervates the vasculature in the head tissue), causing the axons in the vasculature to release vasoactive neuropeptides. These released neuropeptides then activate a series of events, leading to pain. This neurogenic inflammation is blocked by ergot alkaloids and sumatriptan. The blocking mechanism involves 5-HT receptors and is closely related to the 5-HT$_{1D}$ subtype located on the trigeminal nerve vascular fibers (Neurology, 43 (suppl.3): S16-S20, 1993). In fact, sumatriptan has a high affinity for 5-HT$_{1B}$ and 5-HT$_{1D}$ receptors with Ki of 10.3 nM and 5.1 nM, respectively, and this activity exhibits vasoconstriction activity.

5-Hydroxytryptamine receptors, also known as serotonin receptors or 5-HT receptors, are a group of G protein-coupled receptors that appear in the center of the central nervous system and around the peripheral nervous system. They can be divided into seven subfamilies: 5-HT$_1$, 5-HT$_2$, 5-HT$_3$, 5-HT$_4$, 5-HT$_5$, 5-HT$_6$ and 5-HT$_7$, which mediate different physiological activities respectively. Among them, 5-HT$_1$ receptor is the largest family in the 5-HT receptors families. It currently has five subtypes: 5-HT$_{1A}$, 5-HT$_{1B}$, 5-HT$_{1D}$, 5-HT$_{1E}$ and 5-HT$_{1F}$. Kao's research team isolated a human gene that expresses one of these 5-HT$_1$ receptor subtypes (called 5-HT$_{1F}$) (Proc. Natl. Acad. Sci. USA, 90: 408-412, 1993). The pharmacological activity shown by the 5-HT$_{1F}$ receptors is significantly different from any serotonin receptors that have been disclosed. They found that in addition to the above-mentioned strong affinity for 5-HT$_1$B and 5-HT$_{ID}$ receptors, sumatriptan also has an affinity for the receptor subtype, with a Ki of about 23 nM. This suggests that 5-HT$_{1F}$ receptors may play a role in migraine.

5-HT$_{1F}$ receptors are mainly expressed in the mesentery, uterus and brain, but also in various parts of the trigeminal nerve vasculature such as cerebral blood vessels, trigeminal ganglion and trigeminal caudate nucleus, as well as the cerebellum, hippocampus and cerebral neocortex. Like other 5-HT receptors, 5-HT$_{1F}$ receptors are not only expressed in neurons, but also in glial cells. The activation of the presynaptic 5-HT$_{1F}$ receptor can inhibit the release of calcitonin gene-related peptide (CGRP) and block the signal transduction of neurons in the caudate nucleus of the trigeminal nerve, resulting in anti-migraine effects, and this selective 5-HT$_{1F}$ receptor agonism greatly reduces the side effects related to vasoconstriction caused by triptans drugs.

Subsequently, various 5-HT$_{1F}$ receptor agonists with relative selectivity to 5-HT$_{1F}$ receptor subtypes were developed, and this selectivity usually reduces the specific vasoconstrictor activity of other compounds used as potential drugs for the treatment of migraine and related diseases. Therefore, selective 5-$HT_{1F}$ receptor agonists are currently the hotspot of anti-migraine drug research.

After continuous hard research, the inventors have obtained a class of unexpected and new selective 5-$HT_{1F}$ receptor agonists, which has different chemical and receptor binding properties. It can inhibit peptide extravasation and avoid obvious vasoconstriction activity at the same time, so it can be used to treat migraine and other 5-$HT_{1F}$ receptor-related diseases.

Among them, the international application WO 2020038435 A1 discloses the compound 2,4,6-trifluoro-N-(6-(fluoro(1-methylpiperidin-4-ylidene)methyl)pyridin-2-yl)benzamide (compound having formula (I)), which can be used to activate 5-$HT_{1F}$ receptors and inhibit neuronal protein extravasation. However, there is no research on the salt or crystal form of the compound in the prior art.

(I)

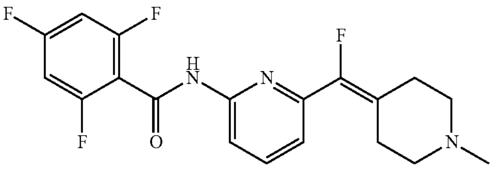

Different salts and solid forms of active pharmaceutical ingredients may have different properties. Different salts and solid forms may have significant differences in appearance, solubility, melting point, dissolution, bioavailability, etc., and may have different effects on the stability, bioavailability and efficacy of the drug. Therefore, salts and/or solid forms of the drug should be fully considered in drug research and development.

When the inventors studied the compound, they found that the compound has poor water solubility and poor druggability. Therefore, in order to find a solid form with better druggability, through a large number of experimental studies, it was found that the physical and chemical properties of different salts change greatly after the compound having formula (I) forms a salt, and the properties of some salts are not better than those of the compounds in the free state. The inventors found that the various properties of the methanesulfonate of the compound having formula (I) prepared according to the method of the present invention can be significantly improved, which is more conducive to formulation development.

SUMMARY OF THE INVENTION

The present invention provides salts of the compound having formula (I), and studies the preparation of the salts, solid forms of the salts, the physical and chemical properties, and the pharmacological properties thereof. It is found that the salts formed by the compound and different acids have very different physical and chemical properties: for example, some salts are less soluble than the compound, some are basically the same as the compound, and some are more soluble than the compound. Among them, the various physicochemical properties of the methanesulfonate of the compound having the formula (I) are better than the compound and other salts. For example, the methanesulfonate crystal form A obtained by the compound having the formula (I) and methanesulfonic acid has higher solubility than the compound having formula (I) and its corresponding benzenesulfonate crystal form A and fumarate crystal form A. Experiments have proved that the methanesulfonate crystal form A of the present invention has better properties, higher solubility, better pharmacokinetic properties, and thus better druggability.

Specifically, the present invention relates to salts of the compound having formula (I), and crystal forms of the salt or the pharmaceutical composition comprising the salts or the crystal forms of the salts in the manufacture of a medicament for preventing, treating or lessening diseases related to 5-$HT_{1F}$ receptors, especially migraine in a patient. The salt in the present invention is methanesulfonate. Further, the salt in the present invention is methanesulfonate crystal form A. The crystal form of the present invention may also be in the form of a solvate, such as a hydrate form.

In one aspect, the present invention provides a salt of a compound having formula (I), (I)

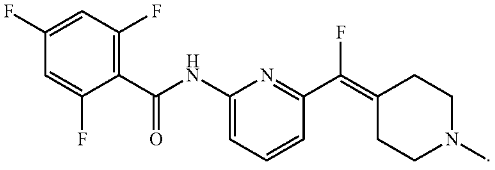

In some embodiments, the salt in the present invention is an organic acid salt or an inorganic acid salt.

In other embodiments, the inorganic acid salt of the present invention includes, but is not limited to, hydrochloride, hydrobromide, phosphate, nitrate or sulfate, etc.; the organic acid salt includes, but is not limited to, acetate, succinate, oxalate, fumarate, maleate, tartrate, citrate, succinate, camphorsulfonate, malonate, benzoate, salicylate, benzenesulfonate, methanesulfonate or p-toluenesulfonate, etc.

In some embodiments, the salt of the compound having formula (I) of the present invention is methanesulfonate.

In some embodiments, the salt of the present invention is methanesulfonate, wherein the methanesulfonate is methanesulfonate crystal form A, and the X-ray powder diffraction pattern of the methanesulfonate crystal form A comprises peaks expressed as 2θ at 9.30°±0.2°, 17.30°±0.2°, 18.55°±0.2°, 19.19°±0.2°, 21.59°±0.2°, 25.63°±0.2°.

In some embodiments, the salt of the present invention is methanesulfonate, wherein the methanesulfonate is methanesulfonate crystal form A, and the X-ray powder diffraction pattern of the methanesulfonate crystal form A comprises peaks expressed as 2θ at 9.30°±0.2°, 12.78°±0.2°, 17.02°±0.2°, 17.30°±0.2°, 17.48°±0.2°, 18.55°±0.2°, 19.19°±0.2°, 20.59°±0.2°, 21.59°±0.2°, 21.99°±0.2°, 23.82°±0.2°, 25.630±0.2°.

In some embodiments, the salt of the present invention is methanesulfonate, wherein the methanesulfonate is methanesulfonate crystal form A, and the X-ray powder diffraction pattern of the methanesulfonate crystal form A comprises peaks expressed as 2θ at 9.30°±0.2°, 12.78°±0.2°, 13.80°±0.2°, 14.00°±0.2°, 14.48°±0.2°, 17.02°±0.2°, 17.30°±0.2°, 17.48°±0.2°, 18.55°±0.2°, 19.19°±0.2°, 20.59°±0.2°, 21.12°±0.2°, 21.59°±0.2°, 21.99°±0.2°, 22.64°±0.2°, 23.23°±0.2°, 23.82°±0.2°, 24.27°±0.2°, 24.88°±0.2°, 25.63°±0.2°, 26.15°±0.2°, 27.00°±0.2°, 27.18°±0.2°, 27.67°±0.2°, 27.95°±0.2°, 28.25°±0.2°, 28.760±0.2°, 29.130±0.2°, 29.610±0.2°, 29.970±0.2°, 30.400±0.2°, 31.210±0.2°, 32.260±0.2°, 32.640±0.2°, 33.42°±0.2°, 34.66°±0.2°, 35.53°±0.2°, 36.94°±0.2°, 37.57°±0.2°, 38.31°±0.2°, 38.86°±0.2°, 39.21°±0.2°, 40.26°±0.2°, 40.75°±0.2°, 42.56°±0.2°, 43.88°±0.2°, 44.44°±0.2°, 45.09°±0.2°, 45.92°±0.2°, 46.65°±0.2°, 51.44°±0.2°.

In some embodiments, the salt of the present invention is methanesulfonate, wherein the methanesulfonate is methanesulfonate crystal form A, and the X-ray powder diffraction pattern of the methanesulfonate crystal form A comprises peaks expressed as 2θ at 9.30°±0.2°, 12.78°±0.2°, 13.80°±0.2°, 14.00°±0.2°, 14.48°±0.2°, 17.02°±0.2°, 17.30°±0.2°, 17.48°±0.2°, 18.55°±0.2°, 19.19°±0.2°, 20.59°±0.2°, 21.12°±0.2°, 21.59°±0.2°, 21.99°±0.2°, 22.64°±0.2°, 23.23°±0.2°, 23.82°±0.2°, 24.27°±0.2°, 24.88°±0.2°, 25.63°±0.2°, 26.15°±0.2°, 27.00°±0.2°, 27.18°±0.2°, 27.67°±0.2°, 27.95°±0.2°, 28.25°±0.2°, 28.76°±0.2°, 29.13°±0.2°, 29.61°±0.2°, 29.97°±0.2°, 30.40°±0.2°, 31.21°±0.2°, 32.26°±0.2°, 32.64°±0.2°, 33.42°±0.2°, 34.66°±0.2°, 35.53°±0.2°, 36.94°±0.2°, 37.57°±0.2°, 38.31°±0.2°, 38.860±0.2°, 39.210±0.2°, 40.26°±0.2°, 40.75°±0.2°, 42.03°±0.2°, 42.56°±0.2°, 43.88°±0.2°, 44.44°±0.2°, 45.09°±0.2°, 45.92°±0.2°, 46.65°±0.2°, 48.21°±0.2°, 50.51°±0.2°, 51.44°±0.2°, 52.56°±0.2°, 55.38°±0.2°, 56.93°±0.2°.

In some embodiments, the salt of the present invention is methanesulfonate, wherein the methanesulfonate is methanesulfonate crystal form A, and the methanesulfonate crystal form A has an X-ray powder diffraction pattern substantially as shown in FIG. 1.

In some embodiments, the salt of the present invention is methanesulfonate, wherein the methanesulfonate is methanesulfonate crystal form A, and the differential scanning calorimeter diagram of the methanesulfonate crystal form A comprises an endothermic peak at 239.57° C.±3° C.

In some embodiments, the salt of the present invention is methanesulfonate, wherein the methanesulfonate is methanesulfonate crystal form A, and the methanesulfonate crystal form A has a differential scanning calorimeter diagram substantially as shown in FIG. 7.

In some embodiments, the salt of the present invention is methanesulfonate, wherein the methanesulfonate is methanesulfonate crystal form A. When the methanesulfonate crystal form A is heated to 200.50° C., the weight loss is 0.2°33%, and the weight loss ratio has an error tolerance of ±0.1%.

In some embodiments, the salt of the present invention is methanesulfonate, wherein the methanesulfonate is methanesulfonate crystal form A, and the methanesulfonate crystal form A has a thermogravimetric analysis diagram substantially as shown in FIG. 13.

In some embodiments, the salt of the present invention is methanesulfonate, wherein the methanesulfonate is methanesulfonate crystal form B, and the X-ray powder diffraction pattern of the methanesulfonate crystal form B comprises peaks expressed as 2θ at 7.57°±0.2°, 7.94°±0.2°, 12.14°±0.2°, 13.60°±0.2°, 17.02°±0.2°, 17.39°±0.2°, 17.85°±0.2°, 21.03°±0.2°, 21.89°±0.2°, 22.67°±0.2°, 23.47°±0.2°.

In some embodiments, the salt of the present invention is methanesulfonate, wherein the methanesulfonate is methanesulfonate crystal form B, and the X-ray powder diffraction pattern of the methanesulfonate crystal form B comprises peaks expressed as 2θ at 7.02°±0.2°, 7.57°±0.2°, 7.94°±0.2°, 9.83°±0.2°, 10.77°±0.2°, 11.68°±0.2°, 12.14°±0.2°, 13.00°±0.2°, 13.60°±0.2°, 13.96°±0.2°, 14.58°±0.2°, 15.07°±0.2°, 15.79°±0.2°, 16.34°±0.2°, 16.66°±0.2°, 17.02°±0.2°, 17.39°±0.2°, 17.85°±0.2°, 18.17°±0.2°, 19.58°±0.2°, 19.98°±0.2°, 21.03°±0.2°, 21.20°±0.2°, 21.89°±0.2°, 22.33°±0.2°, 22.67°±0.2°, 23.47°±0.2°, 23.93°±0.2°, 24.53°±0.2°, 25.47°±0.2°, 25.82°±0.2°, 26.80°±0.2°, 27.30°±0.2°, 28.17°±0.2°, 28.98°±0.2°, 29.59°±0.2°, 29.93°±0.2°, 32.15°±0.2°.

In some embodiments, the salt of the present invention is methanesulfonate, wherein the methanesulfonate is methanesulfonate crystal form B, and the X-ray powder diffraction pattern of the methanesulfonate crystal form B comprises peaks expressed as 2θ at 7.02°±0.2°, 7.57°±0.2°, 7.94°±0.2°, 9.83°±0.2°, 10.77°±0.2°, 11.68°±0.2°, 12.14°±0.2°, 13.00°±0.2°, 13.60°±0.2°, 13.96°±0.2°, 14.58°±0.2°, 15.07°±0.2°, 15.79°±0.2°, 16.34°±0.2°, 16.66°±0.2°, 17.02°±0.2°, 17.39°±0.2°, 17.85°±0.2°, 18.17°±0.2°, 19.58°±0.2°, 19.98°±0.2°, 21.03°±0.2°, 21.20°±0.2°, 21.89°±0.2°, 22.330±0.2°, 22.67°±0.2°, 23.47°±0.2°, 23.93°±0.2°, 24.53°±0.2°, 25.47°±0.2°, 25.82°±0.2°, 26.80°±0.2°, 27.30°±0.2°, 28.17°±0.2°, 28.98°±0.2°, 29.59°±0.2°, 29.93°±0.2°, 31.53°±0.2°, 32.15°±0.2°, 33.50°±0.2°, 35.24°±0.2°.

In some embodiments, the salt of the present invention is methanesulfonate, wherein the methanesulfonate is methanesulfonate crystal form B, and the methanesulfonate crystal form B has an X-ray powder diffraction pattern substantially as shown in FIG. 2.

In some embodiments, the salt of the present invention is methanesulfonate, wherein the methanesulfonate is methanesulfonate crystal form B, and the differential scanning calorimeter diagram of the methanesulfonate crystal form B comprises endothermic peaks at 112.65° C.±3° C. and 239.83° C.±3° C.

In some embodiments, the salt of the present invention is methanesulfonate, wherein the methanesulfonate is methanesulfonate crystal form B, and the methanesulfonate crystal form B has a differential scanning calorimeter diagram substantially as shown in FIG. 8.

In some embodiments, the salt of the present invention is methanesulfonate, wherein the methanesulfonate is methanesulfonate crystal form B. When the methanesulfonate crystal form B is heated to 100.07° C., the weight loss is 5.452%, and the weight loss ratio has an error tolerance of ±0.1%.

In some embodiments, the salt of the present invention is methanesulfonate, wherein the methanesulfonate is methanesulfonate crystal form B, and the methanesulfonate crystal form B has a thermogravimetric analysis diagram substantially as shown in FIG. 14.

In some embodiments, the salt of the present invention is benzenesulfonate, wherein the benzenesulfonate is benzenesulfonate crystal form A, and the X-ray powder diffraction pattern of the benzenesulfonate crystal form A comprises peaks expressed as 2θ at 14.92°±0.2°, 17.17° 0.2°, 19.11°±0.2°, 25.53°±0.2°, 26.67°±0.2°, 27.25°±0.2°, 27.65°±0.2°, 29.70°±0.2°.

In some embodiments, the salt of the present invention is benzenesulfonate, wherein the benzenesulfonate is benzenesulfonate crystal form A, and the X-ray powder diffraction pattern of the benzenesulfonate crystal form A comprises peaks expressed as 2θ at 6.17°±0.2°, 8.01°±0.2°, 13.92°±0.2°, 14.92°±0.2°, 16.26°±0.2°, 17.17°±0.2°, 17.96°±0.2°, 19.11°±0.2°, 20.78°±0.2°, 21.75°±0.2°, 22.32°±0.2°, 23.13°±0.2°, 24.18°±0.2°, 24.85°±0.2°, 25.53°±0.2°, 26.10°±0.2°, 26.67°±0.2°, 27.25°±0.2°, 27.65°±0.2°, 28.40°±0.2°, 29.22°±0.2°, 29.70°±0.2°, 31.09°±0.2°, 32.58°±0.2°, 33.16°±0.2°, 34.14°±0.2°, 35.13°±0.2°, 36.32°±0.2°, 36.85°±0.2°, 37.30°±0.2°.

In some embodiments, the salt of the present invention is benzenesulfonate, wherein the benzenesulfonate is benzenesulfonate crystal form A, and the X-ray powder diffraction pattern of the benzenesulfonate crystal form A comprises peaks expressed as 2θ at 6.17°±0.2°, 8.01°±0.2°, 13.92°±0.2°, 14.92°±0.2°, 16.26°±0.2°, 17.17°±0.2°, 17.96°±0.2°, 19.11°±0.2°, 20.78°±0.2°, 21.75°±0.2°, 22.32°±0.2°, 23.13°±0.2°, 24.18°±0.2°, 24.85°±0.2°, 25.53°±0.2°, 26.10°±0.2°, 26.67°±0.2°, 27.25°±0.2°, 27.65°±0.2°, 28.40°±0.2°, 29.22°±0.2°, 29.70°±0.2°, 31.09°±0.2°, 31.85°±0.2°, 32.58°±0.2°, 33.16°±0.2°, 34.14°±0.2°, 35.13°±0.2°, 35.75°±0.2°, 36.32°±0.2°, 36.85°±0.2°, 37.30°±0.2°, 39.36°±0.2°.

In some embodiments, the salt of the present invention is benzenesulfonate, wherein the benzenesulfonate is benzenesulfonate crystal form A, and the benzenesulfonate crystal form A has an X-ray powder diffraction pattern substantially as shown in FIG. 3.

In some embodiments, the salt of the present invention is benzenesulfonate, wherein the benzenesulfonate is benzenesulfonate crystal form A, and the differential scanning calorimeter diagram of the benzenesulfonate crystal form A comprises endothermic peaks at 112.84° C.±3° C., 121.04° C.±3° C., and 198.05° C.±3° C.

In some embodiments, the salt of the present invention is benzenesulfonate, wherein the benzenesulfonate is benzenesulfonate crystal form A, and the benzenesulfonate crystal form A has a differential scanning calorimeter diagram substantially as shown in FIG. 9.

In some embodiments, the salt of the present invention is benzenesulfonate, wherein the benzenesulfonate is benzenesulfonate crystal form B, and the X-ray powder diffraction pattern of the benzenesulfonate crystal form B comprises peaks expressed as 2θ at 9.48°±0.2°, 11.62°±0.2°, 12.56°±0.2°, 14.87°±0.2°, 19.06°±0.2°, 19.94°±0.2°, 22.33°±0.2°, 25.43°±0.2°.

In some embodiments, the salt of the present invention is benzenesulfonate, wherein the benzenesulfonate is benzenesulfonate crystal form B, and the X-ray powder diffraction pattern of the benzenesulfonate crystal form B comprises peaks expressed as 2θ at 5.88°+0.2°, 9.48°±0.2°, 11.62°±0.2°, 11.81°±0.2°, 12.56°±0.2°, 14.24°±0.2°, 14.87°±0.2°, 16.23°±0.2°, 17.14°±0.2°, 17.40°±0.2°, 17.75°±0.2°, 18.11°±0.2°, 19.06°±0.2°, 19.94°±0.2°, 20.2°±0.2°, 20.76°±0.2°, 20.88°±0.2°, 21.38°±0.2°, 21.68°±0.2°, 22.33°±0.2°, 22.65°±0.2°, 23.12°±0.2°, 23.67°±0.2°, 24.09°±0.2°, 24.33°±0.2°, 24.80°±0.2°, 25.43°±0.2°, 25.83°±0.2°, 26.66°±0.2°, 27.08°±0.2°, 27.69°±0.2°, 27.95°±0.2°, 28.74°±0.2°, 29.21°±0.2°, 29.45°±0.2°, 29.81°±0.2°, 30.04°±0.2°, 30.67°±0.2°, 30.94°±0.2°, 31.22°±0.2°, 31.60°±0.2°, 34.79°±0.2°, 35.15°±0.2°.

In some embodiments, the salt of the present invention is benzenesulfonate, wherein the benzenesulfonate is benzenesulfonate crystal form B, and the X-ray powder diffraction pattern of the benzenesulfonate crystal form B comprises peaks expressed as 2θ at 5.88°±0.2°, 9.48°±0.2°, 11.62°±0.2°, 11.81°±0.2°, 12.56°±0.2°, 14.24°±0.2°, 14.87°±0.2°, 16.23°±0.2°, 17.14°±0.2°, 17.40°±0.2°, 17.75°±0.2°, 18.11°±0.2°, 19.06°±0.2°, 19.94°±0.2°, 20.20°±0.2°, 20.76°±0.2°, 20.88°±0.2°, 21.38°±0.2°, 21.68°±0.2°, 22.33°±0.2°, 22.65°±0.2°, 23.12°±0.2°, 23.67°±0.2°, 24.09°±0.2°, 24.33°±0.2°, 24.80°±0.2°, 25.43°±0.2°, 25.83°±0.2°, 26.66°±0.2°, 27.08°±0.2°, 27.69°±0.2°, 27.95°±0.2°, 28.74°±0.2°, 29.21°±0.2°, 29.45°±0.2°, 29.81°±0.2°, 30.04°±0.2°, 30.67°±0.2°, 30.94°±0.2°, 31.22°±0.2°, 31.60°±0.2°, 31.920±0.2°, 32.60°±0.2°, 34.28°±0.2°, 34.79°±0.2°, 35.15°±0.2°, 36.53°±0.2°, 37.15°±0.2°, 39.71°±0.2°.

In some embodiments, the salt of the present invention is benzenesulfonate, wherein the benzenesulfonate is benzenesulfonate crystal form B, and the benzenesulfonate crystal form B has an X-ray powder diffraction pattern substantially as shown in FIG. 4.

In some embodiments, the salt of the present invention is benzenesulfonate, wherein the benzenesulfonate is benzenesulfonate crystal form B, and the differential scanning calorimeter diagram of the benzenesulfonate crystal form B comprises an endothermic peak at 198.42° C.±3° C.

In some embodiments, the salt of the present invention is benzenesulfonate, wherein the benzenesulfonate is benzenesulfonate crystal form B, and the benzenesulfonate crystal form B has a differential scanning calorimeter diagram substantially as shown in FIG. 10.

In some embodiments, the salt of the present invention is fumarate, wherein the fumarate is fumarate crystal form A, and the X-ray powder diffraction pattern of the fumarate crystal form A comprises peaks expressed as 2θ at 13.51°±0.2°, 16.000 0.2°, 19.47°±0.2°, 19.88°±0.2°, 21.14°±0.2°, 22.74°±0.2°, 24.89°±0.2°, 25.02°±0.2°, 27.27°±0.2°, 28.71°±0.2°, 29.33°±0.2°.

In some embodiments, the salt of the present invention is fumarate, wherein the fumarate is fumarate crystal form A, and the X-ray powder diffraction pattern of the fumarate crystal form A comprises peaks expressed as 2θ at 6.71°±0.2°, 7.94°±0.2°, 11.66°±0.2°, 13.23°±0.2°, 13.51°±0.2°, 14.52°±0.2°, 15.07°±0.2°, 16.00°±0.2°, 17.05°±0.2°, 18.45°±0.2°, 19.08°±0.2°, 19.47°±0.2°, 19.88°±0.2°, 21.14°+0.2°, 22.74°±0.2°, 23.25°±0.2°, 24.89°±0.2°, 25.02°±0.2°, 25.19°±0.2°, 25.69°±0.2°, 25.91°±0.2°, 26.47°±0.2°, 27.27°±0.2°, 27.76°±0.2°, 28.71°±0.2°, 29.33°±0.2°, 31.10°±0.2°, 34.24°±0.2°, 35.24°±0.2°, 36.29°±0.2°, 37.70°±0.2°, 38.64°±0.2°.

In some embodiments, the salt of the present invention is fumarate, wherein the fumarate is fumarate crystal form A, and the X-ray powder diffraction pattern of the fumarate crystal form A comprises peaks expressed as 2θ at 6.71°±0.2°, 7.94°±0.2°, 11.66°±0.2°, 13.23°±0.2°, 13.51°±0.2°, 14.52°±0.2°, 15.07°±0.2°, 16.00°±0.2°, 17.05°±0.2°, 18.45°±0.2°, 19.08°±0.2°, 19.47°±0.2°, 19.88°±0.2°, 20.35°±0.2°, 21.14°±0.2°, 22.74°±0.2°, 23.25°±0.2°, 24.30°±0.2°, 24.89°±0.2°, 25.02°±0.2°, 25.19°±0.2°, 25.69°±0.2°, 25.91°±0.2°, 26.47°±0.2°, 27.27°±0.2°, 27.76°±0.2°, 28.71°±0.2°, 29.33°±0.2°, 31.10°±0.2°, 31.68°±0.2°, 32.52°±0.2°, 34.24°±0.2°, 35.24°±0.2°, 35.84°±0.2°, 36.29°±0.2°, 37.70°±0.2°, 38.64°±0.2°.

In some embodiments, the salt of the present invention is fumarate, wherein the fumarate is fumarate crystal form A, and the fumarate crystal form A has an X-ray powder diffraction pattern substantially as shown in FIG. 5.

In some embodiments, the salt of the present invention is fumarate, wherein the fumarate is fumarate crystal form A, and the differential scanning calorimeter diagram of the fumarate crystal form A comprises an endothermic peak at 202.39° C.±3° C.

In some embodiments, the salt of the present invention is fumarate, wherein the fumarate is fumarate crystal form A, and the fumarate crystal form A has a differential scanning calorimetry diagram substantially as shown in FIG. 11.

In some embodiments, the salt of the present invention is fumarate, wherein the fumarate is fumarate crystal form B, and the X-ray powder diffraction pattern of the fumarate crystal form B comprises peaks expressed as 2θ at 8.53°±0.2°, 8.90°±0.2°, 14.45°±0.2°, 15.32°±0.2°, 15.51°±0.2°, 16.70°±0.2°, 17.07°±0.2°, 19.22°±0.2°, 19.66°±0.2°, 22.41°±0.2°, 23.18°±0.2°, 26.51°±0.2°.

In some embodiments, the salt of the present invention is fumarate, wherein the fumarate is fumarate crystal form B, and the X-ray powder diffraction pattern of the fumarate crystal form B comprises peaks expressed as 2θ at 8.53° 0.2°, 8.90°±0.2°, 11.35°±0.2°, 11.87°±0.2°, 14.45°±0.2°, 15.32°±0.2°, 15.51°±0.2°, 16.15°±0.2°, 16.70°±0.2°, 17.07°±0.2°, 17.76°±0.2°, 18.11°±0.2°, 18.36°±0.2°, 19.22°±0.2°, 19.66°±0.2°, 19.98°±0.2°, 20.20°±0.2°, 20.50°±0.2°, 21.22°±0.2°, 22.41°±0.2°, 23.18°±0.2°, 23.40°±0.2°, 23.99°±0.2°, 25.10°±0.2°, 26.05°±0.2°, 26.51°±0.2°, 26.79°±0.2°, 27.62°±0.2°, 27.83°±0.2°, 28.87°±0.2°, 30.63°±0.2°, 31.33°±0.2°, 31.85°±0.2°, 32.49°±0.2°.

In some embodiments, the salt of the present invention is fumarate, wherein the fumarate is fumarate crystal form B, and the X-ray powder diffraction pattern of the fumarate crystal form B comprises peaks expressed as 2θ at 8.53°±0.2°, 8.90°+0.2°, 11.35°±0.2°, 11.87°±0.2°, 14.45°±0.2°, 15.32°±0.2°, 15.51°±0.2°, 16.15°±0.2°, 16.70°±0.2°, 17.07°±0.2°, 17.76°±0.2°, 18.11°±0.2°, 18.36°±0.2°, 19.22°±0.2°, 19.66°±0.2°, 19.98°±0.2°, 20.20°±0.2°, 20.50°±0.2°, 21.22°±0.2°, 22.41°±0.2°, 23.18°±0.2°, 23.40°±0.2°, 23.99°±0.2°, 25.10°±0.2°, 26.05°±0.2°, 26.51°±0.2°, 26.79°±0.2°, 27.62°±0.2°, 27.83°±0.2°, 28.87°±0.2°, 29.85°±0.2°, 30.63°±0.2°, 31.33°±0.2°, 31.85°±0.2°, 32.49°±0.2°, 34.63°±0.2°, 36.71°±0.2°.

In some embodiments, the salt of the present invention is fumarate, wherein the fumarate is fumarate crystal form B, and the fumarate crystal form B has an X-ray powder diffraction pattern substantially as shown in FIG. 6.

In some embodiments, the salt of the present invention is fumarate, wherein the fumarate is fumarate crystal form B, and the differential scanning calorimeter diagram of the fumarate crystal form B comprises an endothermic peak at 219.88° C.±3° C.

In some embodiments, the salt of the present invention is fumarate, wherein the fumarate is fumarate crystal form B, and the fumarate crystal form B has a differential scanning calorimetry diagram substantially as shown in FIG. 12.

In another aspect, the present invention relates to a pharmaceutical composition comprising any one of the salts of the invention, and a pharmaceutically acceptable carrier, excipient, diluent, adjuvant or a combination thereof.

In one aspect, the present invention relates to use of the salt or the pharmaceutical composition disclosed herein in the manufacture of a medicament for preventing, treating or lessening diseases related to 5-$HT_{1F}$ receptors in a subject.

In some embodiments, the diseases related to 5-$HT_{1F}$ receptors are migraine, general pain, trigeminal neuralgia, toothache or temporomandibular joint dysfunction pain, autism, obsessive-compulsive disorder, panic disorder, depression, social phobia, anxiety, generalized anxiety disorder, sleep disorder, post-traumatic syndrome, chronic fatigue syndrome, premenstrual syndrome or post-luteal syndrome, borderline personality disorder, disruptive behavior disorder, impulse control disorder, attention deficit hyperactivity disorder, alcoholism, tobacco abuse, mutism, trichotillomania, excessive appetite, anorexia nervosa, premature ejaculation, erectile dysfunction, memory loss or dementia.

In one aspect, the present invention relates to a method of preventing, treating or lessening diseases related to 5-$HT_{1F}$ receptors in a subject comprising administering to the subject a therapeutically effective amount of the salt or the pharmaceutical composition disclosed herein.

In some embodiments, the diseases related to 5-$HT_{1F}$ receptors are migraine, general pain, trigeminal neuralgia, toothache or temporomandibular joint dysfunction pain, autism, obsessive-compulsive disorder, panic disorder, depression, social phobia, anxiety, generalized anxiety disorder, sleep disorder, post-traumatic syndrome, chronic fatigue syndrome, premenstrual syndrome or post-luteal syndrome, borderline personality disorder, disruptive behavior disorder, impulse control disorder, attention deficit hyperactivity disorder, alcoholism, tobacco abuse, mutism, trichotillomania, excessive appetite, anorexia nervosa, premature ejaculation, erectile dysfunction, memory loss or dementia.

In one aspect, the present invention relates to the salt or the pharmaceutical composition disclosed herein for use in preventing, treating or lessening diseases related to 5-$HT_{1F}$ receptors in a subject.

In some embodiments, the diseases related to 5-$HT_{1F}$ receptors are migraine, general pain, trigeminal neuralgia, toothache or temporomandibular joint dysfunction pain, autism, obsessive-compulsive disorder, panic disorder, depression, social phobia, anxiety, generalized anxiety disorder, sleep disorder, post-traumatic syndrome, chronic fatigue syndrome, premenstrual syndrome or post-luteal syndrome, borderline personality disorder, disruptive behavior disorder, impulse control disorder, attention deficit hyperactivity disorder, alcoholism, tobacco abuse, mutism, trichotillomania, excessive appetite, anorexia nervosa, premature ejaculation, erectile dysfunction, memory loss or dementia.

In another aspect, the present invention relates to use of the salt or the pharmaceutical composition disclosed herein in the manufacture of a medicament for activating 5-$HT_{1F}$ receptors in a subject.

In another aspect, the present invention relates to a method of activating 5-$HT_{F}$ receptors in a subject comprising administering to the subject a therapeutically effective amount of the salt or the pharmaceutical composition disclosed herein.

In another aspect, the present invention relates to the salt or the pharmaceutical composition disclosed herein for use in activating 5-$HT_{1F}$ receptors in a subject.

In another aspect, the present invention also relates to the preparation method of the salt of the compound having formula (I) or its crystal form.

The solvent used in the preparation method of the salt or its crystal form of the invention is not particularly restricted, and any solvent which dissolves the starting material to a degree and does not affect its properties is contained in the present invention. Additionally, many similar modifications in the art, equivalent replacements, or solvent, solvent composition and the solvent composition with different proportions which are equivalent to those described in the invention, are all deemed to be included in the present invention. The present invention gives the preferred solvent for each reaction step.

The preparation of the salt or its crystal form of the present invention will be described in detail in the examples section. Meanwhile, the present invention provides pharmacological property test experiments (for example, pharmacokinetic experiment), solubility test, stability test, hygroscopicity test, etc. of the salt or its crystal form. Experiments have proved that the methanesulfonate crystal form A of the present invention has unexpected technical advantages:

1. The methanesulfonate crystal form A has good stability, for example, no or almost no hygroscopicity. It will not change when placed at room temperature. It is also very stable under high temperature, high humidity and light experimental conditions, and there is basically no change in appearance, purity and crystal form.
2. The methanesulfonate crystal form A has higher solubility than the compound having formula (I) and other salts, such as benzenesulfonate crystal form A and fumarate crystal form A.
3. Compared with the compound having formula (I), the methanesulfonate crystal form A has a higher blood concentration and exposure in beagle dogs, and thus has better pharmacokinetic properties.

Therefore, the methanesulfonate crystal form A of the present invention has better biological activity, higher stability, and is more suitable for pharmaceutical use.

DEFINITIONS AND GENERAL TERMINOLOGY

Unless otherwise indicated, all technical and scientific terms used in the present invention have the same meaning as commonly understood by one of ordinary skilled in the art to which this invention pertains. All patents and publications referred to herein are incorporated by reference in their entirety. Although any methods and materials similar or identical to those described herein may be used in the practice or testing of the invention, but the methods, apparatus and materials described in the invention are preferred.

"Crystal form" or "crystalline form" refers to a solid having a highly regular chemical structure, including, but not limited to, mono- or multi-component crystals, and/or polymorphic compounds of compounds, solvates, hydrates, clathrates, co-crystals, salts, salt solvates, salt hydrates. The crystalline form of the material can be obtained by a number of methods known in the field. Such methods include, but are not limited to, melt crystallization, melt cooling, solvent crystallization, crystallization in defined space, for example, in nanopores or capillaries, on a surface or template, for example, on a polymer, in the presence of additives such as co-crystallization counterions, removing solvent, dehydration, rapid evaporation, rapid cooling, slow cooling, vapor diffusion, sublimation, reaction crystallization, anti-solvent addition, grinding and solvent drop milling.

"amorphous" or "amorphous form" refers to a substance formed when the mass point (molecule, atom, ion) of a substance is arranged in a non-periodic manner in a three-dimensional space, characterized by an X-ray powder diffraction pattern with diffuse undisturbed peaks. Amorphization is a special physical form of solid matter, its local and orderly structural features suggest that it is inextricably linked with the crystalline material. The amorphous form of the material can be obtained by a number of methods known in the field. Such methods include, but are not limited to, quenching, anti-solvent flocculation, ball milling, spray drying, freeze drying, wet granulation and solid dispersion techniques.

"Solvent" refers to a substance (typically a liquid) that is capable of completely or partially dissolving another substance (typically a solid). Solvents for use in the practice of this invention include, but are not limited to, water, acetic acid, acetone, acetonitrile, benzene, chloroform, carbon tetrachloride, dichloromethane, dimethylsulfoxide, 1,4-dioxane, ethanol, ethyl acetate, dimethyl carbonate, butanol, t-butanol, N, N-dimethylacetamide, N, N-dimethylformamide, formamide, formic acid, heptane, hexane, isopropanol, methanol, methyl ethyl ketone, mesitylene, nitromethane, polyethylene glycol, propanol, pyridine, tetrahydrofuran, toluene, xylene, mixtures thereof, and the like.

"Anti-solvent" refers to a fluid that promotes the precipitation of a product (or product precursor) from a solvent. The anti-solvent may comprise a cold gas, or a fluid that promotes the precipitation of the product by chemical reaction or reduces the solubility of the product in the solvent; it may be the same liquid as the solvent but at a different temperature, or it may be a liquid different from the solvent.

"Solvate" refers to a compound that having a solvent on a surface, in a lattice, or both on a surface and in a lattice. The solvent can be water, acetic acid, acetone, acetonitrile, benzene, chloroform, carbon tetrachloride, dichloromethane, dimethylsulfoxide, 1,4-dioxane, ethanol, ethyl acetate, dimethyl carbonate, butanol, t-butanol, N, N-dimethylacetamide, N, N-dimethylformamide, formamide, formic acid, heptane, hexane, isopropanol, methanol, methyl ethyl ketone, methyl pyrrolidone, mesitylene, nitromethane, polyethylene glycol, propanol, pyridine, tetrahydrofuran, toluene, xylene, mixtures thereof, and the like. A specific example of the solvate is a hydrate in which the solvent on the surface, in the lattice or both on the surface and in the lattice is water. On the surface, in the lattice or both on the surface and in the lattice of the substance, the hydrate may or may not have any solvent other than water.

Crystal form can be identified by a variety of technical means, such as X-ray powder diffraction (XRPD), infrared absorption spectroscopy (IR), melting point method, differential scanning calorimetry (DSC), thermogravimetric analysis (TGA), Nuclear magnetic resonance, Raman spectroscopy, X-ray single crystal diffraction, dissolution calorimetry, scanning electron microscopy (SEM), quantitative analysis, solubility and dissolution rate.

X-ray powder diffraction (XRPD) can detect changes in crystal form, crystallinity, crystal state and other information. It is a common means for identifying crystal form. The peak position of the XRPD pattern primarily depends on the structure of the crystal form and is relatively insensitive to the experimental details, and its relative peak height depends on many factors associated with sample preparation and instrument geometry. Thus, in some embodiments, the crystalline form of the present invention is characterized by an XRPD pattern having certain peak positions, which is substantially as shown in the XRPD pattern provided in the drawings of the present invention. At the same time, the 2θ of the XRPD pattern can be measured with an experimental error. The measurement of 2θ of the XRPD pattern may be slightly different between the different instruments and between the different samples. Therefore, the value of 2θ cannot be regarded as absolute. According to the condition of the instrument used in this test, the diffraction peak has an error tolerance of ±0.2°.

Differential Scanning Calorimetry (DSC) is a technique of measuring the change of energy difference between a sample and an inert reference (commonly used $\alpha$-$Al_2O_3$) varied with temperature by continuously heating or cooling under program control The endothermic peak height of the DSC curve depends on many factors associated with sample preparation and instrument geometry, while the peak position is relatively insensitive to experimental details. Thus, in some embodiments, the crystal form of the present invention is characterized by an DCS diagram having certain peak positions, which is substantially as shown in the DCS diagram provided in the drawings of the present invention. At the same time, the DCS diagram may have experimental errors. The peak position and peak value of DCS diagram may be slightly different between the different instruments and between the different samples. Therefore, the peak position or the peak value of the DSC endothermic peak cannot be regarded as absolute. According to the condition of the instrument used in this test, the endothermic peak has an error tolerance of ±3° C.

Thermogravimetric analysis (TGA) is a technique for measuring the change in the mass of a substance with temperature under the control of a program. It is suitable for examining the process of the solvent loss or the samples sublimation and decomposition. It can be presumed that the crystal contains crystal water or crystallization solvent. The quality variety of the TGA curve shown depends on a number of factors, containing the sample preparation and the instrument. The quality change from the TGA test varies slightly between the different instruments and between the different samples. According to the condition of the instrument used in this test, there is an error tolerance of ±0.1% for the mass change.

In the context of the present invention, the 26 values in the X-ray powder diffraction pattern are in degrees (°).

The term "substantially as shown in the figure" refers to at least 50%, or at least 60%, or at least 70%, or at least 80%, or at least 80%, or at least 90%, or at least 95%, or at least 99% of the peaks are shown in the X-ray powder diffraction pattern or DSC pattern or Raman spectra pattern or infrared spectra pattern.

The "peak" refers to a feature that a person skilled in the art can recognize without belonging to background noise when referring to a spectrum or/and data that appears in the figure.

The present invention relates to the salts of 2,4,6-trifluoro-N-(6-(fluoro(1-methylpiperidin-4-ylidene)methyl) pyridin-2-yl)benzamide and/or its crystal forms. They exist in a substantially pure crystalline form.

"Substantially pure" means that a crystal form is substantially free of another or more crystal forms, that means the purity of the crystalline form is at least 80%, or at least 85%, or at least 90%, or at least 93%, or at least 95%, or at least 98%, or at least 99%, or at least 99.5%, or at least 99.6%, or at least 99.7%, or at least 99.8%, or at least 99.9%; or a crystal form contains other crystal forms, and the percentage of the other crystal forms in the total volume or total weight of the crystal forms is less than 20%, or less than 10%, or less than 5%, or less than 3%, or less than 1%, or less than 0.5%, or less than 0.1%, or less than 0.01%.

"Substantially free" means that the percentage of one or more other crystalline forms in the total volume or total weight of the crystalline forms is less than 20%, or less than 10%, or less than 5%, or less than 4%, or less than 3%, or less than 2%, or less than 1%, or less than 0.5%, or less than 0.1%, or less than 0.01%.

"Relative strength" means the ratio of the intensity of the other peaks to the intensity of the first strong peak when the intensity of the first strong peak in all the diffraction peaks of the X-ray powder diffraction pattern (XRPD) is 100%.

In the context of the present invention, when used or whether or not used the word, such as "about", it means within a given value or range of 10% or less, appropriately within 5%, especially within 1%. Or, for those of ordinary skill in the art, the term "about" means within an acceptable standard error range of the mean value. When a number with an N value is made public, any number within N+/−1%, N+/−2%, N+/−3%, N+/−5%, N+/−7%, N+/−8%, or N+/−10% is opened clearly, wherein "+/−" means plus or minus.

In the present invention, "room temperature" refers to the temperature from about 10° C. to about 40° C. In some embodiments, "room temperature" refers to a temperature from about 20° C. to about 30° C.; in other embodiments, "room temperature" refers to 20° C., 22.5° C., 25° C., 27.5° C., and the like.

PHARMACEUTICAL COMPOSITIONS, FORMULATIONS, ADMINISTRATION AND USES OF THE SALTS OR ITS CRYSTAL FORMS OF THE PRESENT INVENTION

The pharmaceutical composition of the present invention is characterized by comprising the salts and/or its crystal forms of the compound having Formula (I), and pharmaceutically acceptable carriers, adjuvants, or excipients. The amount of the salt or its crystal form of the compound in the pharmaceutical composition of the present invention can be effectively and detectably for treating or lessening the 5-$HT_{1F}$ receptor-related diseases in the patient, especially migraine. The pharmaceutical composition of the present invention may also optionally contain other therapeutic and/or preventive components.

Suitable carriers, adjuvants and excipients are well known to those skilled in the art and are described in detail in, for example, Ansel H C et al., Ansel's Pharmaceutical Dosage Forms and Drug Delivery Systems (2004) Lippincott, Williams & Wilkins, Philadelphia; Gennaro A. R. et al., Remington: The Science and Practice of Pharmacy (2000) Lippincott, Williams & Wilkins, Philadelphia; and Rowe R C, Handbook of Pharmaceutical Excipients (2005) Pharmaceutical Press, Chicago.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

Various carriers used in formulating pharmaceutically acceptable compositions and known techniques for the preparation thereof are disclosed in Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which are incorporated by reference herein. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

The pharmaceutical compositions of the invention are prepared using techniques and methods known to those skilled in the art. Some of the methods commonly used in the art are described in Remington's Pharmaceutical Sciences (Mack Publishing Company).

In another aspect, the present invention is related to a method for preparing the pharmaceutical composition, the pharmaceutical composition contains the salt of the compound disclosed herein or its crystal form and pharmaceutically acceptable excipient, carrier, adjuvant, vehicle or a combination thereof, the method comprises mixing various ingredients. The pharmaceutical composition containing the salt of the compound disclosed herein or its crystal form can be prepared at for example environment temperature and under barometric pressure.

The salt of the compound or its crystal form of the invention will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

In one embodiment, the therapeutic methods disclosed herein comprise administrating to a patient in need of the treatment a safe and effective amount of the salt of compound of the invention or its crystal form or the pharmaceutical composition containing the salt of compound of the invention or its crystal form. The various embodiments of the present invention include the treatment of the diseases mentioned in the present invention by administrating to a patient in need a safe and effective amount of the salt of compound of the invention or its crystal form or the pharmaceutical composition containing the salt of compound of the invention or its crystal form.

In one embodiment, the salt of the compound of the present invention or its crystal form or the pharmaceutical composition comprising the salt of the compound of the present invention or its crystal form may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. In one embodiment, the salt of the compound of the present invention or its crystal form or the pharmaceutical composition comprising the salt of the compound of the present invention or its crystal form may be administered orally. In another embodiment, the salt of the compound of the present invention or its crystal form or the pharmaceutical composition comprising the salt of the compound of the present invention or its crystal form may be administered by inhalation. In another embodiment, the salt of the compound of the present invention or its crystal form or the pharmaceutical composition comprising the salt of the compound of the present invention or its crystal form may be administered intranasally.

In one embodiment, the salt of the compound of the present invention or its crystal form or the pharmaceutical composition comprising the salt of the compound of the present invention or its crystal form may be administered once, or a number of doses are administered at varying intervals of time for a given period of time according to a dosing regimen. For example, doses may be administered once, twice, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for the salt of the compound of the present invention or its crystal form or the pharmaceutical composition comprising the salt of the compound of the present invention or its crystal form depend on the pharmacokinetic properties of that compound, such as absorption, distribution, and half-life, which can be determined by the skilled artisan. In addition, suitable dosing regimens, including the duration of implementation of such regimens, for the salt of the compound of the present invention or its crystal form or the pharmaceutical composition comprising the salt of the compound of the present invention or its crystal form depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

The salt of the compound of the present invention or its crystal form may be administered either simultaneously with, or before or after, one or more other therapeutic agents. The salt of the compound of the present invention or its crystal form may be administered separately, by the same or different route of administration, or together in the same pharmaceutical composition as the other agents.

The term "therapeutically effective amount" as used herein, refers to the total amount of each active component that is sufficient to show a meaningful patient benefit. For example, an amount sufficient to treat, cure or alleviate the symptoms of the disease is administered or brought into balance in the body. The effective amount required for a particular treatment plan depends on many factors, including the disease being treated, the severity of the disease, the activity of the used specific drug, the method of administration, the clearance rate of the specific drug, the duration of treatment, the combination of drugs, age, weight, gender, diet and patient's health, etc. For a description of other factors to be considered for "therapeutically effective amount" in this field, please refer to Gilman et al., eds., Goodman and Gilman's: The Pharmacological Bases of Therapeutics, 8th ed., Pergamon Press, 1990; Remington's Pharmaceutical Sciences, 17th ed., Mack Publishing Company, Easton, Pa., 1990.

The compound having formula (I) is preferably formulated in an unit dosage form, each dosage containing about 0.001-100 mg of active ingredient, and more often about 1.0-30 mg of active ingredient. The term "unit dosage form" refers to a physically separate unit suitable as an unit dose for human patients and other mammals. Each unit contains a predetermined amount of active ingredient calculated to produce the desired therapeutic effect and suitable pharmaceutically acceptable excipients as described above.

The active compound is usually effective over a wide dosage range. For example, the daily dose is generally about 0.0001-30 mg/kg body weight. For adult treatment, a particularly preferred dose (single dose or divided dose) is about 0.1-15 mg/kg/day. However, it should be understood that the amount of compound actually administered will be determined by the attending physician according to the relevant circumstances, including the disease being treated, the route of administration chosen, the one or more compounds to be actually administered, the age, weight and response of the specific patient, and the severity of the patient's symptoms. Therefore, the above dosage range should not limit the scope of the present invention in any way. In some cases, a dosage level lower than the lower limit of the above-mentioned dosage range may be more appropriate, while in other cases, a higher dosage that does not produce any side effects can be used, provided that this larger dose is first divided into several smaller doses for administration throughout the day.

The optimal therapeutically effective amount to be administered can be easily determined by those skilled in the art, and basically varies according to the strength of the formulation, the mode of administration, and the progress of the disease or condition to be treated. In addition, factors related to the specific subject being treated include the subject's age, weight, diet, and administration time leading to the need to adjust the dosage to an appropriate therapeutically effective level.

The term "administration" refers to the provision of a therapeutically effective amount of a drug to an individual. The modes of administration include oral, sublingual, intravenous, subcutaneous, transdermal, intramuscular, intradermal, intrathecal, supradural, intraocular, intracranial, inhaled, rectal, vaginal and the like. Dosage forms include ointment, lotion, tablet, capsule, pill, dispersible powder, granule, suppository, sublimed pill, lozenge, injection, sterile solution or non-aqueous solution, suspension, emulsion, patch, etc. The active ingredient is compounded with a non-toxic pharmaceutically acceptable carrier (such as glucose, lactose, gum arabic, gelatin, mannitol, starch paste, magnesium trisilicate, talc, corn starch, keratin, silica gel, potato starch, urea, dextran, etc.).

The preferred route of administration will vary with clinical characteristics, and the change of dose must depend on the condition of the patient being treated. The doctor will determine the appropriate dose according to the individual patient. The therapeutically effective amount per unit dose depends on body weight, physiological function and the chosen vaccination schedule. The compound per unit dose refers to the weight of the compound per administration, excluding the weight of the carrier (the drug contains the carrier).

The salt of the compound provided by the present invention or its crystal form and pharmaceutical composition can be used in the manufacture of a medicament for preventing, treating or lessening diseases related to 5-$HT_{1F}$ receptors, especially in the manufacture of a medicament for preventing, treating or lessening migraine. It can also be used in the manufacture of a medicament for activating 5-$HT_{1F}$ receptors.

Specifically, the amount of the compound in the pharmaceutical composition of the present invention can effectively and detectably activate the 5-$HT_{1F}$ receptors selectively, and the salt or crystal form of the compound of the present invention can be used as a medicine for treating 5-$HT_{1F}$ receptor-related diseases such as migraine.

The salt of the compound of the present invention or its crystal form can be useful for, but is not limited to, preventing, treating or lessening diseases related to 5-$HT_{1F}$ receptors by administering to the patient the salt of the compound of the present invention or its crystal form or the pharmaceutical composition in an effective amount. The diseases related to 5-$HT_{1F}$ receptors further include, but are not limited to, migraine, general pain, trigeminal neuralgia, toothache or temporomandibular joint dysfunction pain, autism, obsessive-compulsive disorder, panic disorder, depression, social phobia, anxiety, generalized anxiety disorder, sleep disorder, post-traumatic syndrome, chronic fatigue syndrome, premenstrual syndrome or post-luteal syndrome, borderline personality disorder, disruptive behavior disorder, impulse control disorder, attention deficit hyperactivity disorder, alcoholism, tobacco abuse, mutism, trichotillomania, excessive appetite, anorexia nervosa, premature ejaculation, erectile dysfunction, memory loss and dementia.

An "effective amount" or "effective dose" of the salt of the compound of the present invention or its crystal form or pharmaceutically acceptable composition is an amount that is effective in treating or lessening the severity of one or more of the aforementioned disorders. The salt of the compound of the present invention or its crystal form or pharmaceutically acceptable composition, according to the method disclosed herein, may be administered using any amount and any route of administration, which is effective for treating or lessening the severity of the disorder or disease. The exact amount required will vary from subject to subject, depending on the species, age, and general condition of the subject, the severity of the infection, the particular agent, its mode of administration, and the like. The salt of the compound of the present invention or its crystal form or pharmaceutically acceptable composition can also be administered with one or more other therapeutic agents as discussed above.

Besides being useful for human treatment, the salt of the compound of the present invention or its crystal form or pharmaceutically composition is also useful for veterinary treatment of animals such as companion animals, exotic animals and mammals in farm animals. In other embodiments, the animals disclosed herein include horses, dogs, and cats.

EXAMPLES

Figure 1:
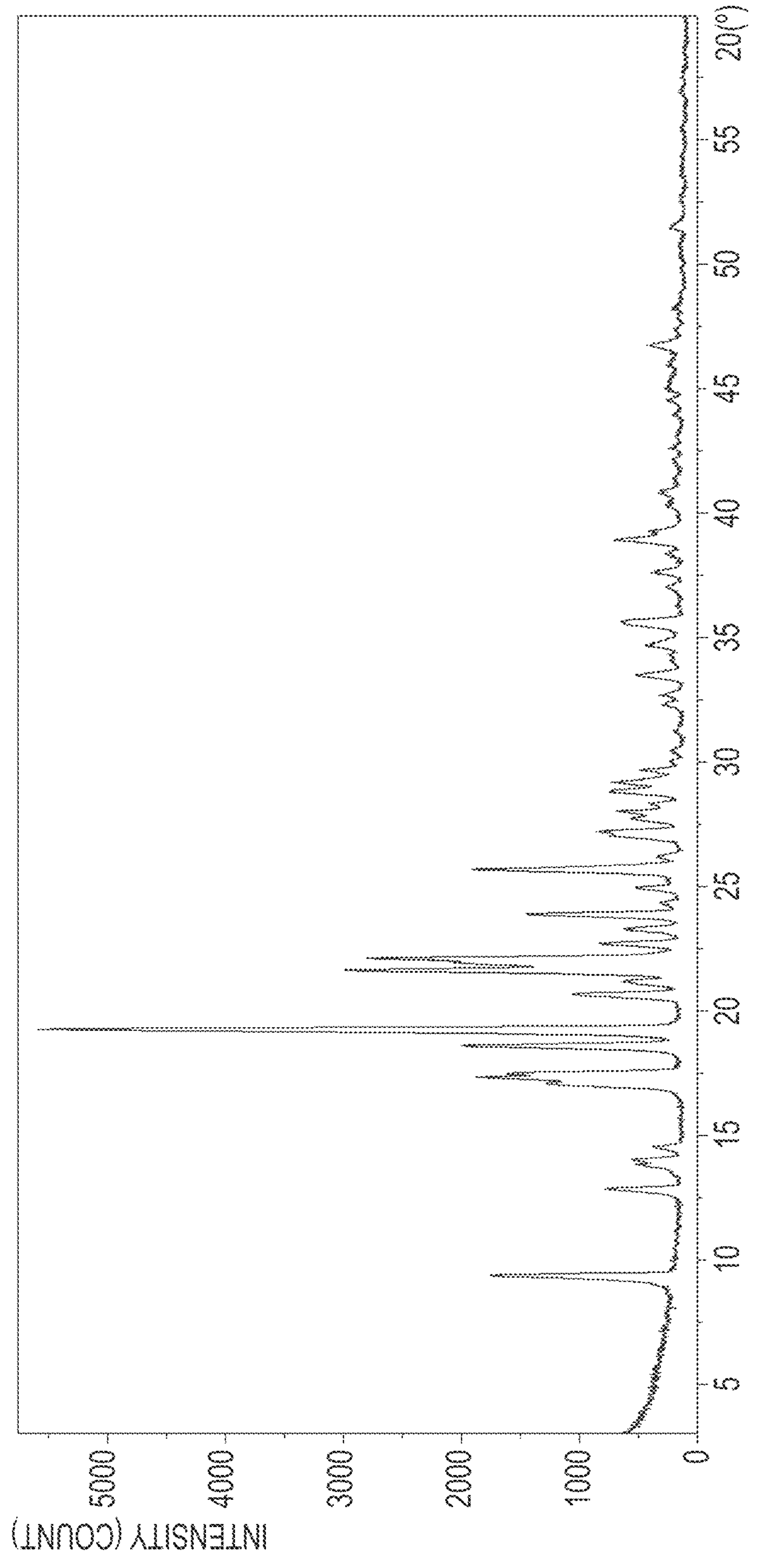
FIG. 1 is an X-ray powder diffraction (XRPD) pattern of the methanesulfonate crystal form A of the compound having formula (I).
Figure 2:
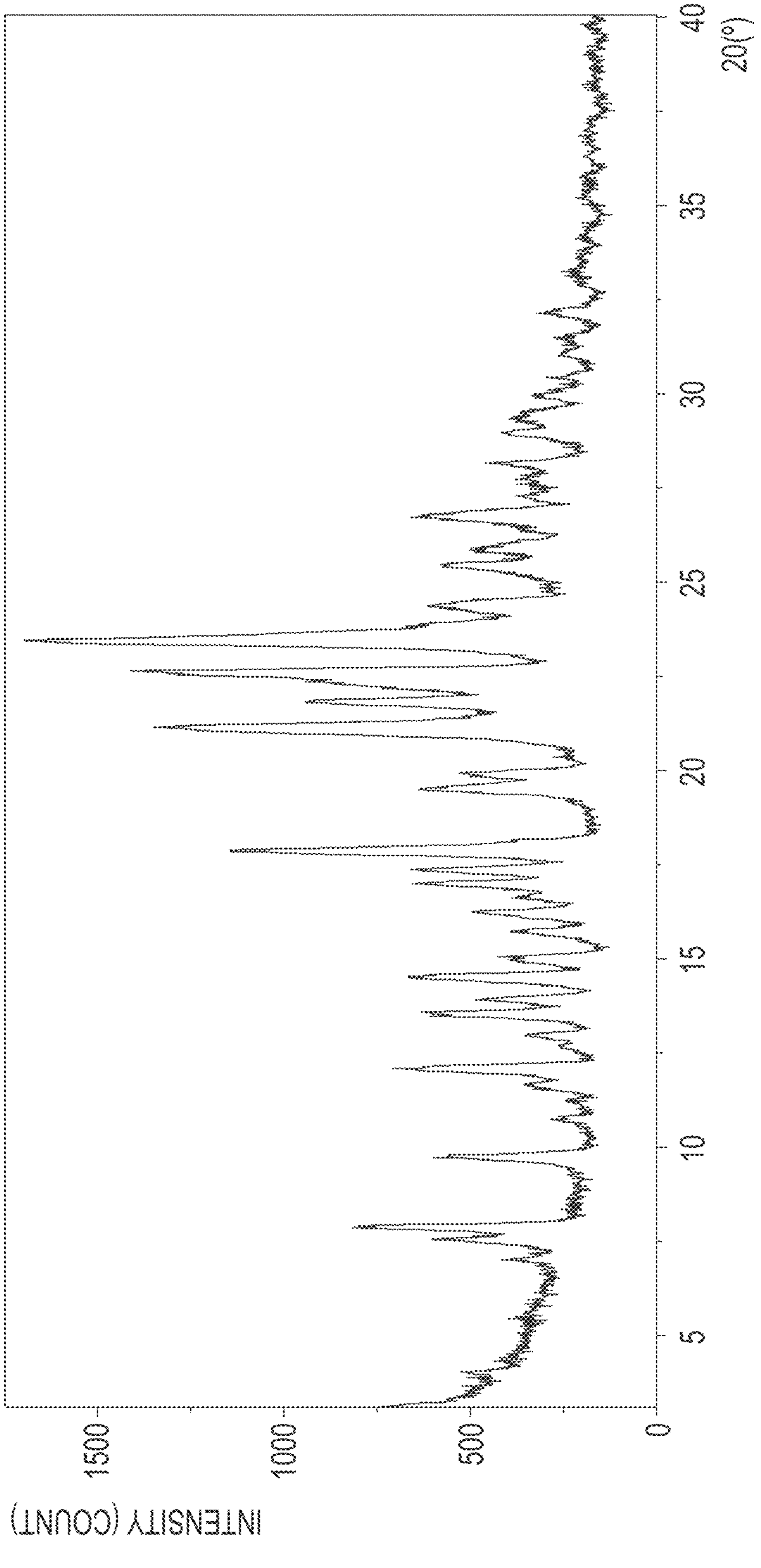
FIG. 2 is an X-ray powder diffraction (XRPD) pattern of the methanesulfonate crystal form B of the compound having formula (I).
Figure 3:
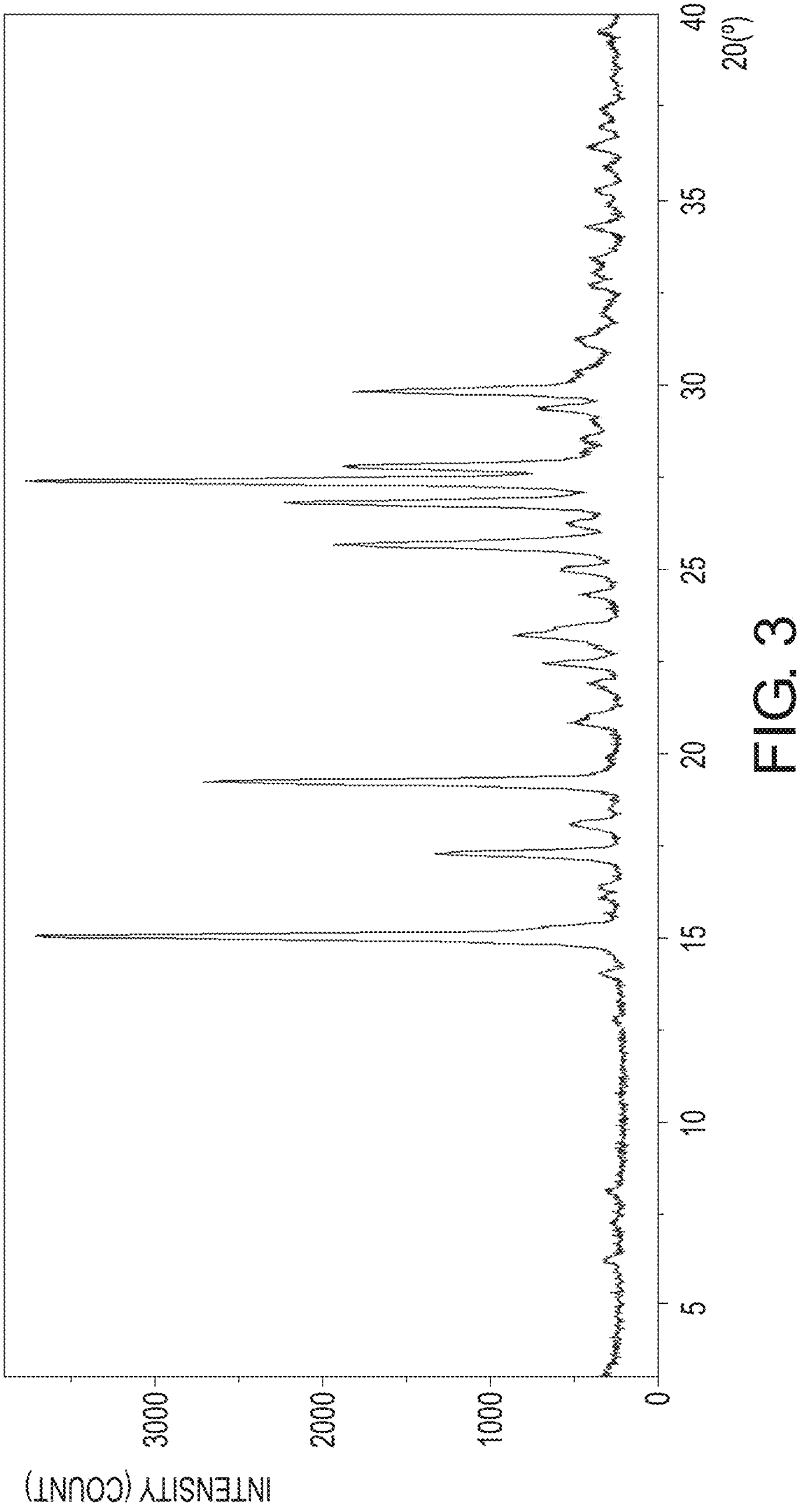
FIG. 3 is an X-ray powder diffraction (XRPD) pattern of the benzenesulfonate crystal form A of the compound having formula (I).
Figure 4:
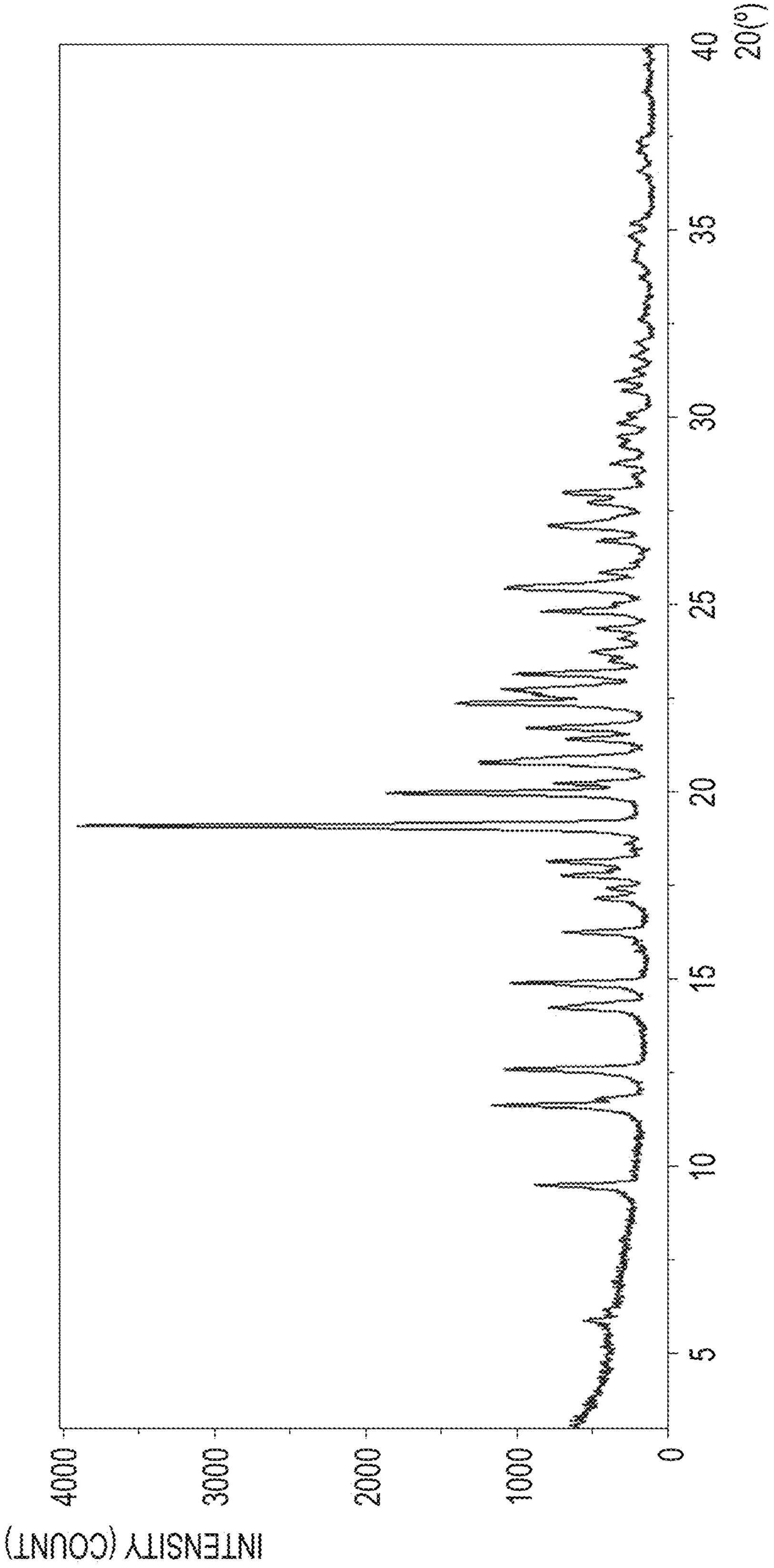
FIG. 4 is an X-ray powder diffraction (XRPD) pattern of the benzenesulfonate crystal form B of the compound having formula (I).
Figure 5:
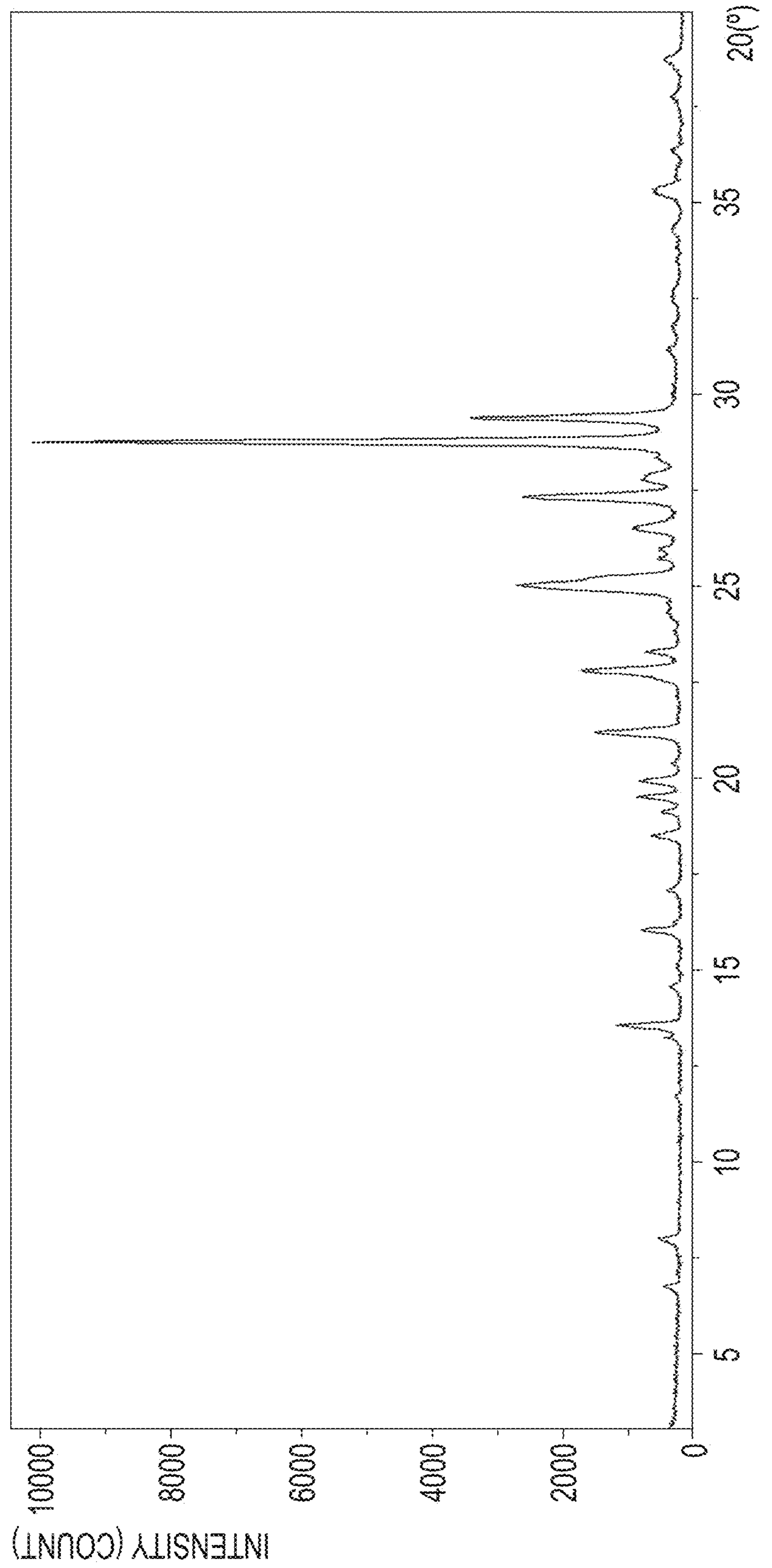
FIG. 5 is an X-ray powder diffraction (XRPD) pattern of the fumarate crystal form A of the compound having formula (I).
Figure 6:
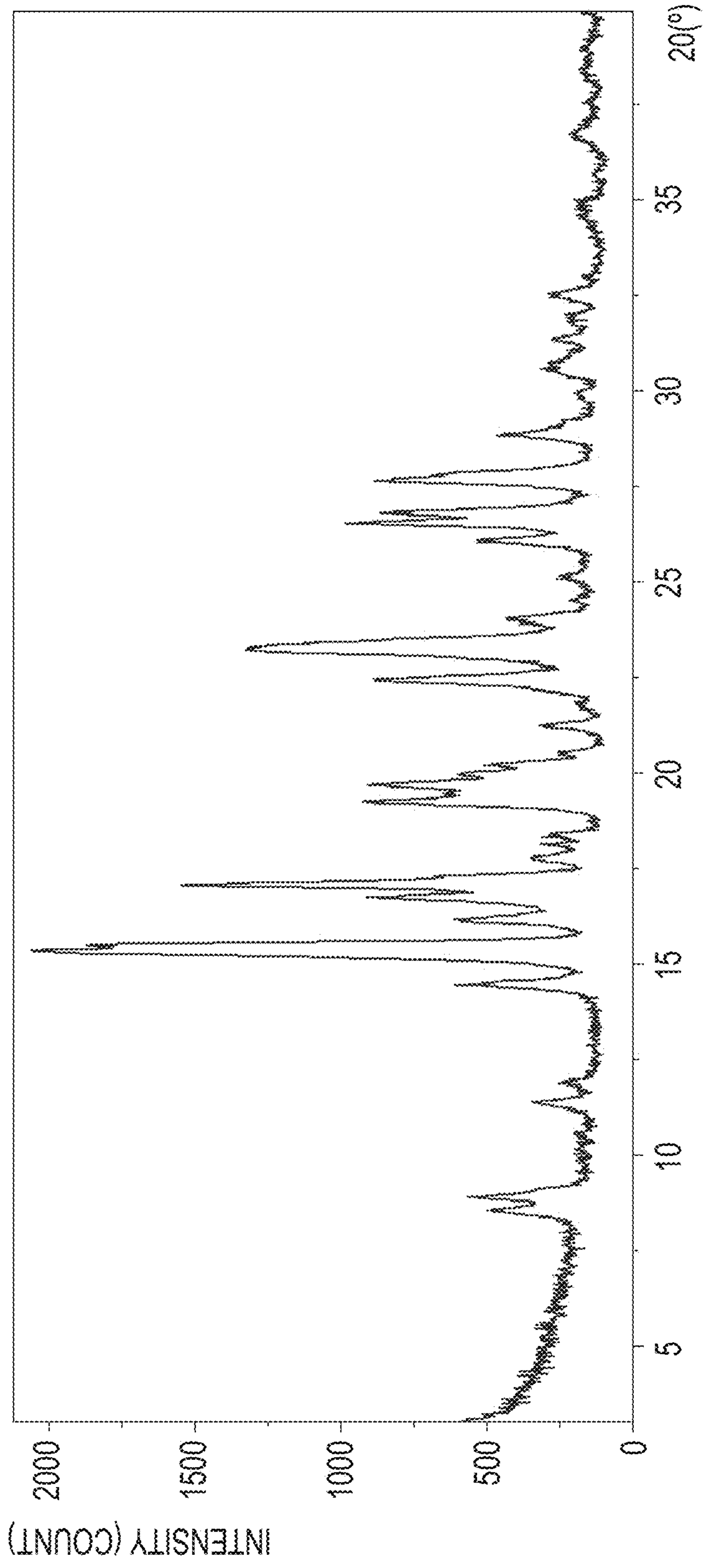
FIG. 6 is an X-ray powder diffraction (XRPD) pattern of the fumarate crystal form B of the compound having formula (I).

The invention will now be further described by way of example without limiting the invention to the described examples.

The X-ray powder diffraction analysis method used in the present invention was an Empyrean diffractometer, and an X-ray powder diffraction pattern was obtained using Cu-Kα radiation (45 KV, 40 mA). The powdery sample was prepared as a thin layer on a monocrystalline silicon sample rack and placed on a rotating sample stage, analyzed with a step size of 0.01670 in the range of 3°-40° or 3-60°. Data Collector software was used to collect data, HighScore Plus software was used to process data, Data Viewer software was used to read data.

The differential scanning calorimetry (DSC) analysis method used in the present invention was performing a differential scanning calorimetry analysis using a TA Q2000 module with a thermal analysis controller. Data were collected and analyzed using TA Instruments Thermal Solutions software. Approximately 1-5 mg of the sample was accurately weighed into a specially crafted aluminum crucible with a lid and analyzed from room temperature to about 300° C. using a linear heating device at 10° C./min. During use, the DSC chamber was purged with dry nitrogen.

The thermogravimetric analysis (TGA) method used in the present invention was performing a thermogravimetric analysis using a TA Q500 module with a thermal analysis controller. Data were collected and analyzed using TA Instruments Thermal Solutions software. Approximately 10-30 mg of the sample was placed into a platinum crucible and analyzed from room temperature to about 300° C. using a linear heating device at 10° C./min. During use, the TGA chamber was purged with dry nitrogen.

The solubility of the present invention was determined using an Agilent 1200 High Performance Liquid Chromatograph DAD/VWD detector with an Agilent XDB-C18 model (4.6×50 mm, 5 μm). Detection wavelength was 266 nm, flow rate was 1.0 mL/min, the column temperature was 35° C., mobile phase A: acetonitrile: 0.01 M ammonium acetate=10:90 (V:V), analysis methods: acetonitrile: mobile phase A=70:30 (V:V), running time was 10 minutes.

EXAMPLES

Compound having formula (I): 2,4,6-trifluoro-N-(6-(fluoro(1-methylpiperidin-4-ylidene)methyl)pyridin-2-yl) benzamide. For the specific synthesis method, refer to Example 12 in International Application WO 2020038435 A1.

EXAMPLES

Example 1: The Methanesulfonate Crystal Form a of the Present Invention

1. Preparation of Methanesulfonate Crystal Form A

The compound having formula (I) (75.86 g) was added to a 1 L flask at room temperature, then ethyl acetate (455 mL) was added. The mixture was heated to 80° C. and stirred to dissolve, then a solution of methanesulfonic acid (20.22 g) in ethyl acetate (300 mL) was slowly added dropwise to the aforementioned ethyl acetate solution at 80° C. using a peristaltic pump to crystallize. After the addition, the temperature was lowered to room temperature, and the mixture was stirred continuously for 2 h. The resulting mixture was filtered, the obtained solid was rinsed with ethyl acetate (75 mL×2), and dried under vacuum at 50° C. to obtain 90.66 g of white solid powder, which is the methanesulfonate crystal form A, with a yield of 95.41%.

2. Identification of Methanesulfonate Crystal Form A (1) Analysis and identification by Empyrean X-ray powder diffraction (XRPD): Cu-Kα radiation was used and the pattern comprised the following characteristic peaks expressed as 2θ at: 9.30°, 12.78°, 13.80°, 14.00°, 14.48°, 17.02°, 17.30°, 17.48°, 18.55°, 19.19°, 20.59°, 21.12°, 21.59°, 21.99°, 22.64°, 23.23°, 23.82°, 24.27°, 24.88°, 25.63°, 26.15°, 27.00°, 27.18°, 27.67°, 27.95°, 28.25°, 28.76°, 29.13°, 29.61°, 29.97°, 30.40°, 31.21°, 32.26°, 32.64°, 33.42°, 34.66°, 35.53°, 36.94°, 37.57°, 38.31°, 38.86°, 39.21°, 40.26°, 40.75°, 42.03°, 42.56°, 43.88°, 44.44°, 45.09°, 45.92°, 46.65°, 48.21°, 50.51°, 51.44°, 52.56°, 55.38°, 56.93°, with an error tolerance of ±0.2°.

(2) Analysis and identification by TA Q2000 Differential Scanning Calorimetry (DSC): the scanning speed was 10° C./min and the diagram comprised an endothermic peak of 239.57° C. There was an error tolerance of ±3° C.

(3) Analysis and identification by Thermogravimetric Analysis (TGA) using TA Q500: the heating rate was 10° C./min, and when heated to 200.50° C., the weight loss was 0.2033%, and there was an error tolerance of ±0.1%.

Example 2: The Methanesulfonate Crystal Form B of the Present Invention

1. Preparation of Methanesulfonate Crystal Form B

To a mixed solvent of dichloromethane (1 mL) and water (100 μL) was added the methanesulfonate crystal form A (110 mg) of the compound having formula (I) at room temperature. The mixture was stirred and dissolved at room temperature until clear, and then the solvent was slowly volatilized at room temperature. After the solvent was volatilized to dryness, 98 mg of white solid powder was obtained, which is the methanesulfonate crystal form B, with a yield of about 89.09%.

2. Identification of Methanesulfonate Crystal Form B (1) Analysis and identification by Empyrean X-ray powder diffraction (XRPD): Cu-Kα radiation was used and the pattern comprised the following characteristic peaks expressed as 2θ at: 7.02°, 7.57°, 7.94°, 9.83°, 10.77°, 11.68°, 12.14°, 13.00°, 13.60°, 13.96°, 14.58°, 15.07°, 15.79°, 16.34°, 16.66°, 17.02°, 17.39°, 17.85°, 18.17°, 19.58°, 19.98°, 21.03°, 21.20°, 21.89°, 22.33°, 22.67°, 23.47°, 23.93°, 24.53°, 25.47°, 25.82°, 26.80°, 27.30°, 28.17°, 28.98°, 29.59°, 29.93°, 31.53°, 32.15°, 33.50°, 35.24°, with an error tolerance of ±0.2°.

(2) Analysis and identification by TA Q2000 Differential Scanning Calorimetry (DSC): the scanning speed was 10° C./min and the diagram comprised endothermic peaks of 112.65° C. and 239.83° C. There was an error tolerance of ±3° C.

(3) Analysis and identification by Thermogravimetric Analysis (TGA) using TA Q500: the heating rate was 10° C./min, and when heated to 100.07° C., the weight loss was 5.452%, and there was an error tolerance of ±0.1%.

Example 3: The Benzenesulfonate Crystal Form a of the Present Invention

1. Preparation of Benzenesulfonate Crystal Form A

To the compound having formula (I) (388 mg) were added isopropanol (4 mL) and benzenesulfonic acid aqueous solution (425 mg, 75 mass %), and the mixture was stirred at room temperature. The turbidity increased, and the crystallization was obvious. The mixture was stirred continuously overnight. The resulting mixture was filtered, the obtained solid was rinsed with n-heptane (2 mL), and dried under vacuum at 50° C. to obtain a white solid powder, which is the benzenesulfonate crystal form A, with a yield of 83%.

2. Identification of Benzenesulfonate Crystal Form A (1) Analysis and identification by Empyrean X-ray powder diffraction (XRPD): Cu-Kα radiation was used and the pattern comprised the following characteristic peaks expressed as 2θ at: 6.17°, 8.01°, 13.92°, 14.92°, 16.26°, 17.17°, 17.96°, 19.11°, 20.78°, 21.75°, 22.32°, 23.13°, 24.18°, 24.85°, 25.53°, 26.10°, 26.67°, 27.25°, 27.65°, 28.40°, 29.22°, 29.70°, 31.09°, 31.85°, 32.58°, 33.16°, 34.14°, 35.13°, 35.75°, 36.32°, 36.85°, 37.30°, 39.36°, with an error tolerance of ±0.2°.

(2) Analysis and identification by TA Q2000 Differential Scanning Calorimetry (DSC): the scanning speed was 10° C./min and the diagram comprised endothermic peaks of 112.84° C., 121.04° C. and 198.05° C. There was an error tolerance of +3° C.

Example 4: The Benzenesulfonate Crystal Form B of the Present Invention

1. Preparation of Benzenesulfonate Crystal Form B

To the compound having formula (I) (1.14 g) was added ethyl acetate (12 mL), and the mixture was heated to 60° C. to dissolve. Benzenesulfonic acid aqueous solution (0.76 g, 75 mass %) was added dropwise, and the mixture was stirred continuously. The turbidity increased, and the crystallization was obvious. After cooling to room temperature, the mixture was continued to stir overnight. The resulting mixture was filtered, the obtained solid was rinsed with n-heptane (10 mL), and dried under vacuum at 50° C. to obtain a white solid powder, which is the benzenesulfonate crystal form B, with a yield of 93%.

2. Identification of Benzenesulfonate Crystal Form B (1) Analysis and identification by Empyrean X-ray powder diffraction (XRPD): Cu-Kα radiation was used and the pattern comprised the following characteristic peaks expressed as 2θ at: 5.88°, 9.48°, 11.62°, 11.81°, 12.56°, 14.24°, 14.87°, 16.23°, 17.14°, 17.40°, 17.75°, 18.11°, 19.06°, 19.94°, 20.20°, 20.76°, 20.88°, 21.38°, 21.68°, 22.33°, 22.65°, 23.12°, 23.67°, 24.09°, 24.33°, 24.80°, 25.43°, 25.83°, 26.66°, 27.08°, 27.69°, 27.95°, 28.74°, 29.21°, 29.45°, 29.81°, 30.04°, 30.67°, 30.94°, 31.22°, 31.60°, 31.92°, 32.60°, 34.28°, 34.79°, 35.15°, 36.53°, 37.15°, 39.71°, with an error tolerance of ±0.2°.

(2) Analysis and identification by TA Q2000 Differential Scanning Calorimetry (DSC): the scanning speed was 10° C./min and the diagram comprised an endothermic peak of 198.42° C. There was an error tolerance of ±3° C.

Example 5: The Fumarate Crystal Form a of the Present Invention

1. Preparation of Fumarate Crystal Form A

To the compound having formula (I) (388 mg) was added ethyl acetate (8 mL), and the mixture was heated to 50° C. and stirred to dissolve, then fumaric acid (245 mg) was added and stirred. After cooling to room temperature, the mixture was stirred continuously. The turbidity increased, and the crystallization was obvious. The mixture was continued to stir overnight. The resulting mixture was filtered, and the obtained solid was dried under vacuum at 50° C. to obtain a white solid powder, which is the fumarate crystal form A, with a yield of 85%.

2. Identification of Fumarate Crystal Form A (1) Analysis and identification by Empyrean X-ray powder diffraction (XRPD): Cu-Kα radiation was used and the pattern comprised the following characteristic peaks expressed as 2θ at: 6.71°, 7.94°, 11.66°, 13.23°, 13.51°, 14.52°, 15.07°, 16.00°, 17.05°, 18.45°, 19.08°, 19.47°, 19.88°, 20.35°, 21.14°, 22.74°, 23.25°, 24.30°, 24.89°, 25.02°, 25.19°, 25.69°, 25.91°, 26.47°, 27.27°, 27.76°, 28.71°, 29.33°, 31.10°, 31.68°, 32.52°, 34.24°, 35.24°, 35.84°, 36.29°, 37.70°, 38.64°, with an error tolerance of ±0.2°.

(2) Analysis and identification by TA Q2000 Differential Scanning Calorimetry (DSC): the scanning speed was 10° C./min and the diagram comprised an endothermic peak of 202.39° C. There was an error tolerance of +3° C.

Example 6: The Fumarate Crystal Form B of the Present Invention

1. Preparation of Fumarate Crystal Form B

To the compound having formula (I) (380 mg) was added ethyl acetate (8 mL), and the mixture was heated to 60° C. and stirred to dissolve, then fumaric acid (69.6 mg) was added and stirred. The turbidity increased, and the crystallization was obvious. After cooling to room temperature, the mixture was continued to stir overnight. The resulting mixture was filtered, and the obtained solid was dried under vacuum at 50° C. to obtain a white solid powder, which is the fumarate crystal form B, with a yield of 88%.

2. Identification of Fumarate Crystal Form B (1) Analysis and identification by Empyrean X-ray powder diffraction (XRPD): Cu-Kα radiation was used and the pattern comprised the following characteristic peaks expressed as 2θ at: 8.53°, 8.90°, 11.35°, 11.87°, 14.45°, 15.32°, 15.51°, 16.15°, 16.70°, 17.07°, 17.76°, 18.11°, 18.36°, 19.22°, 19.66°, 19.98°, 20.20°, 20.50°, 21.22°, 22.41°, 23.18°, 23.40°, 23.99°, 25.10°, 26.05°, 26.51°, 26.79°, 27.62°, 27.83°, 28.87°, 29.85°, 30.63°, 31.33°, 31.85°, 32.49°, 34.63°, 36.71°, with an error tolerance of ±0.2°.

(2) Analysis and identification by TA Q2000 Differential Scanning Calorimetry (DSC): the scanning speed was 10° C./min and the diagram comprised an endothermic peak of 219.88° C. There was an error tolerance of ±3° C.

Example 7 Pharmacokinetic Experiment of the Salt or its Crystal Form of the Present Invention The inventors conducted a pharmacokinetic evaluation of the salt or its crystal form of the present invention in Beagle dogs. Among them, the animal information is shown in Table 1.

TABLE 1

Information table of the tested animal of the present invention

| Germline | Grade | Gender | Weight | Age | Source |
|---|---|---|---|---|---|
| Beagle dog | Ordinary | Male | 8~12 kg | 6-12 months | Beijing Max Biotechnology Co., Ltd. |

Test Method

The test sample (i.e., the salt or crystal form of the present invention, or the compound having formula (I) of the present invention) was filled into capsules for oral administration. The animals were fasted for 12 h before the administration, and they had free drinking water. Capsules containing test samples were administered orally at a dose of 5 mg/kg. After administration, intravenous blood was collected at the following time points (about 0.15 mL of blood taken): 0.25, 0.5, 1.0, 2.0, 4.0, 6.0, 8.0 and 24 h. EDTA-$K_2$ was added as an anticoagulant in the blood collection tube in advance, the blood sample was centrifuged at 12,000 rpm for 2 minutes, the plasma was collected, and stored at −20° C. or −70° C.

After processing the plasma samples collected above (after the frozen plasma was thawed at room temperature, it was whirled for 5 minutes to mix well, then 20 μL of plasma was taken, 120 μL of acetonitrile solution containing internal standard was added, the mixture was whirled for 5 minutes to mix well, and centrifuged at 4,000 rpm for 5 minutes, then 100 μL of the supernatant was taken, 130 μL of methanol-water (V/V=1/1) was added to mix well), a standard curve with a suitable range was established according to the concentration of the test sample, and the LC-MS/MS with AB SCIEX API5500 was used, the concentration of the test sample in the plasma sample was determined in the MRM mode, and quantitative analysis was performed. Pharmacokinetic parameters were calculated according to drug concentration-time curve using a non-compartmental method by WinNonLin 6.3 software. Results are as shown in Table 2.

TABLE 2

Pharmacokinetic data of the salt or its crystal form of the present invention

| Test sample | $T_{max}$ (h) | $C_{max}$ (ng/ml) | $AUC_{last}$ (h * ng/ml) |
|---|---|---|---|
| Example 1 (methanesulfonate crystal form A) | 0.667 | 99.9 | 238 |
| Compound having formula (I) | 3.67 | 32.8 | 117 |

Conclusion:

It can be seen from Table 2 that, compared with the compound having formula (I), the methanesulfonate crystal form A of the present invention has higher plasma concentration, greater exposure, and better pharmacokinetic properties in Beagle dogs.

Example 8 the Stability Experiment of the Salt or its Crystal Form of the Present Invention (1) High temperature experiment: an appropriate amount of a batch of test samples were taken into flat weighing bottles, and spread into a thin layer ≥5 mm thick. The above weighing bottles were placed in a constant temperature box at 40° C.±2° C./75%±5% RH and/or 60° C.±2° C./75%±5% RH for 30 days, the samples were taken on the 5th, 10th, and 30th days, and tested according to the key stability inspection items: the color changes of the samples were observed, the purities of the samples were checked by HPLC, and the structure of the samples were analyzed by X-ray powder diffraction.

(2) High humidity experiment: an appropriate amount of a batch of test samples were taken into flat weighing bottles, and spread into a thin layer ≥5 mm thick. The above weighing bottles were placed at 25° C., RH 75%±5% or RH 90%±5% RH for 30 days, the samples were taken on the 5th, 10th, and 30th days, and tested according to the key stability inspection items: the color changes of the samples were observed, the purities of the samples were checked by HPLC, and the structures of the samples were analyzed by X-ray powder diffraction.

(3) Light experiment: an appropriate amount of a batch of test samples were taken into flat weighing bottles, and spread into a thin layer ≥5 mm thick. The above weighing bottles were placed and opened in a light box (with UV) at the illuminance 4500±500 lx, UV light ≤0.7 w·h/$m^2$ for 30 days, the samples were taken on the 5th, 10th, and 30th days, and tested according to the key stability inspection items: the color changes of the samples were observed, the purities of the samples were checked by HPLC, and the structures of the samples were analyzed by X-ray powder diffraction.

Among them, the stability experiment results of the methanesulfonate crystal form A of the present invention are as follows:

1. The changes of appearance and purities of the test samples in the stability experiment are as shown in Table 3.

TABLE 3

The changes of appearance and purities of methanesulfonate crystal form A of the present invention in the stability experiment

| Condition | | High temperature (40° C.) | | | High temperature (60° C.) | | | High humidity (25° C., RH 75% ± 5%) | | | High humidity (25° C., RH 90% ± 5%) | | | Light | | |
|---|---|---|---|---|---|---|---|---|---|---|---|---|---|---|---|---|
| Project | 0 day | the 5th day | the 10th day | the 30th day | the 5th day | the 10th day | the 30th day | the 5th day | the 10th day | the 30th day | the 5th day | the 10th day | the 30th day | the 5th day | the 10th day | the 30th day |
| Appearance | white solid | white solid | white solid | white solid | white solid | white solid | white solid | white solid | white solid | white solid | white solid | white solid | white solid | white solid | white solid | white solid |
| Purity (%) | 99.66 | 99.73 | 99.72 | 99.79 | 99.72 | 99.74 | 99.8 | 99.71 | 99.74 | 99.77 | 99.68 | 99.71 | 99.72 | 99.59 | 99.43 | 97.66 |

Figure 15:
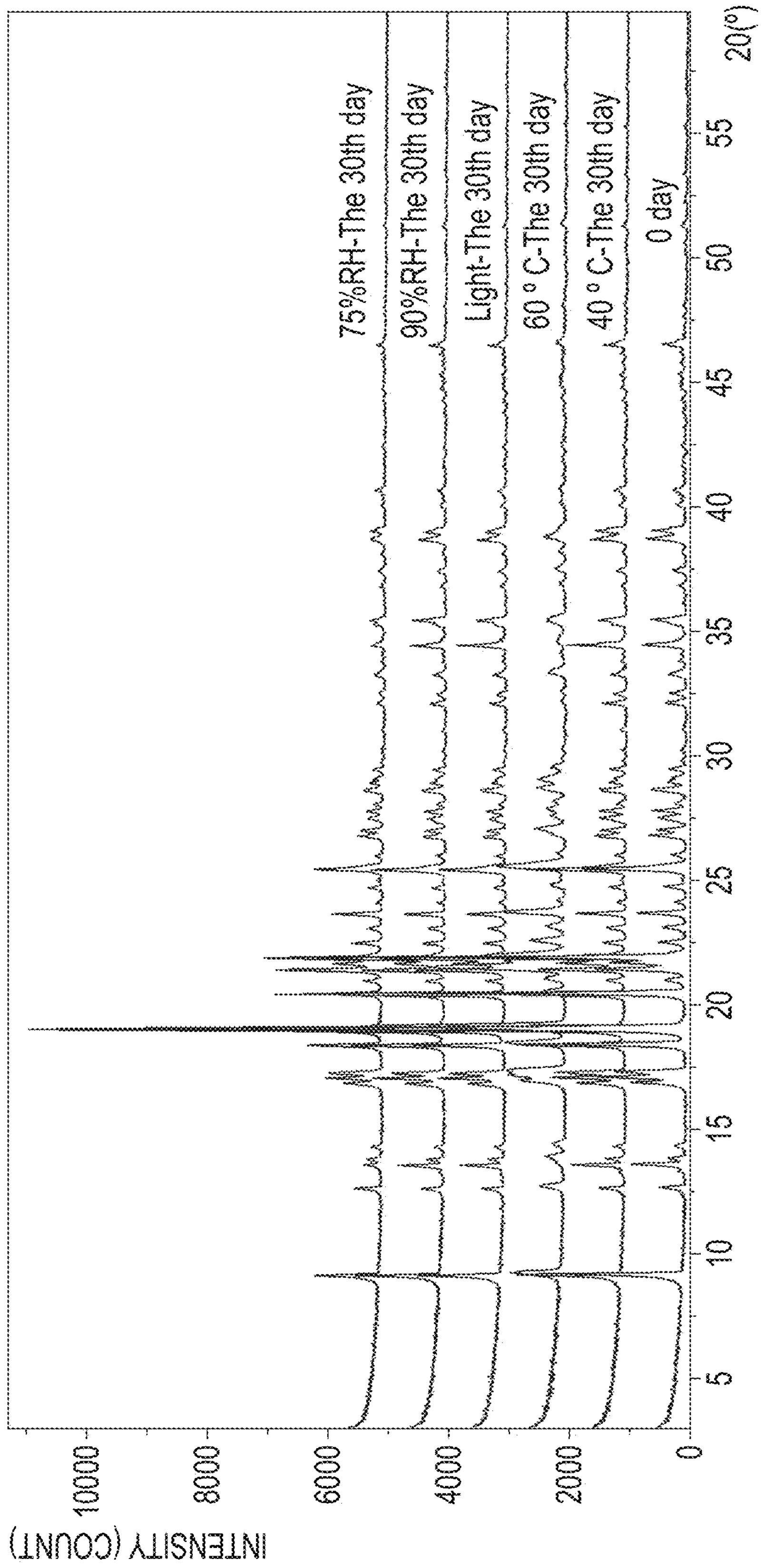
FIG. 15 is a comparison of X-ray powder diffraction (XRPD) patterns of the stability experiment process of the methanesulfonate crystal form A of the compound having formula (I) under high temperature, high humidity and light experimental conditions in Example 8.

2. The X-ray powder diffraction change of the methanesulfonate crystal form A of the present invention under the experimental conditions of high temperature, high humidity and light is basically shown in FIG. 15.

It can be known from the experimental results that under the experimental conditions of high temperature, high humidity and light, the appearance, purity and crystal form of the methanesulfonate salt crystal form A of the present invention have no obvious changes. Therefore, the methanesulfonate crystal form A of the present invention has good stability under the experimental conditions of high temperature, high humidity and light and is suitable for pharmaceutical use.

Example 9 Hygroscopicity Experiment of the Salt or its Crystal Form of the Present Invention Test Method:

1) A dry stoppered glass weighing bottle (outer diameter of 50 mm, height of 15 mm) was taken the day before, and placed in a 25° C.±1° C. constant temperature desiccator (a saturated ammonium chloride solution was placed at the bottom), and the weighing bottle was weighed accurately ($m_1$).

2) An appropriate amount of the test sample was taken, and spread flat in the above weighing bottle, the thickness of the test sample was generally about 1 mm, and the weighing bottle was weighed accurately ($m_2$).

3) The weighing bottle was open and placed under the above constant temperature and humidity conditions with the bottle cap for 24 hours.

4) The bottle cap was covered on the weighing bottle, and weighed accurately ($m_3$), and calculate: the percentage increase in weight $\%=(m_3-m_2)/(m_2-m_1)\times100\%$ 5) The hygroscopicity results are judged as shown in Table 4.

TABLE 4

Judgment of the hygroscopicity results

| The hygroscopic feature | | The hygroscopic weight gain |
|---|---|---|
| 1 | Deliquescence | Absorb enough water to form a liquid |
| 2 | Highly hygroscopicity | Not less than 15% |
| 3 | Hygroscopicity | Less than 15% but not less than 2% |
| 4 | Lightly hygroscopicity | Less than 2% but not less than 0.2% |
| 5 | No or almost no hygroscopicity | Less than 0.2% |

Conclusion:

The methanesulfonate crystal form A of the present invention has no or almost no hygroscopicity, and is not susceptible to deliquescence under the influence of high humidity.

Example 10 Solubility Experiment of the Salt or its Crystal Form of the Present Invention The test sample was taken into 37° C. organic ultrapure water to prepare a supersaturated solution. After shaking for 24 h, the mixture was filtered with an aqueous filter membrane to obtain the filtrate. The solubility of the test sample in water was detected by HPLC. Results are as shown in Table 5.

TABLE 5

Experimental data of solubility of the salt or its crystal form of the present invention

| Test sample | Concentration of compound having formula (I) in saturated aqueous solution (mg/mL) |
|---|---|
| Example 1 (methanesulfonate crystal form A) | 300.88 |
| Example 3 (benzenesulfonate crystal form A) | 1.89 |
| Example 5 (fumarate crystal form A) | 3.39 |
| Compound having formula (I) | 2.59 |

Conclusion:

The experimental results show that, compared with the compound having formula (I), the benzenesulfonate crystal form A and the fumarate crystal form A of the compound having formula (I), the methanesulfonate crystal form A of the present invention has higher solubility in water, so it has better medicinal properties and is more suitable for formulation development.

The foregoing description is merely a basic illustration of the present invention and any equivalent transformation made in accordance with the technical solution of the present invention is intended to be within the scope of the present invention.

Reference throughout this specification to “an embodiment”, “some embodiments”, “one embodiment”, “another example”, “an example”, “a specific example”, or “some examples” means that a particular feature, structure, material, or characteristic described in connection with the embodiment or example is included in at least one embodiment or example of the present disclosure. Thus, the appearances of the above terms throughout this specification are not necessarily referring to the same embodiment or example of the present disclosure. Furthermore, the particular features, structures, materials, or characteristics may be combined in any suitable manner in one or more embodiments or examples. In addition, those skilled in the art can integrate and combine different embodiments, examples or the features of them as long as they are not contradictory to one another.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

The invention claimed is:

1. A salt of a compound having formula (I),

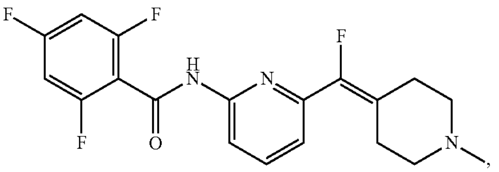

(I)

wherein the salt is methanesulfonate, wherein the methanesulfonate is methanesulfonate crystal form A, and the X-ray powder diffraction pattern of the methanesulfonate crystal form A comprises peaks expressed as 2θ at 9.30°±0.2°, 17.30°±0.2°, 18.55°±0.2°, 19.19°±0.2°, 21.59°±0.2°, 25.63°±0.2°.

2. The salt of claim 1, wherein the methanesulfonate is methanesulfonate crystal form A, and the X-ray powder diffraction pattern of the methanesulfonate crystal form A comprises peaks expressed as 2θ at 9.30°±0.2°, 12.78°±0.2°, 17.02°±0.2°, 17.30°±0.2°, 17.48°±0.2°, 18.55°±0.2°, 19.19°±0.2°, 20.59°±0.2°, 21.59°±0.2°, 21.99°±0.2°, 23.82°±0.2°, 25.63°±0.2°.

3. The salt of claim 1, wherein the methanesulfonate is methanesulfonate crystal form A, and the X-ray powder diffraction pattern of the methanesulfonate crystal form A comprises peaks expressed as 2θ at 9.30°±0.2°, 12.78°±0.2°, 13.80°±0.2°, 14.00°±0.2°, 14.48°±0.2°, 17.02°±0.2°, 17.30°±0.2°, 17.48°±0.2°, 18.55°±0.2°, 19.19°±0.2°, 20.59°±0.2°, 21.12°±0.2°, 21.59°±0.2°, 21.99°±0.2°, 22.64°±0.2°, 23.23°±0.2°, 23.82°±0.2°, 24.27°±0.2°, 24.88°±0.2°, 25.63°±0.2°, 26.15°±0.2°, 27.00°±0.2°, 27.18°±0.2°, 27.67°±0.2°, 27.95°±0.2°, 28.25°±0.2°, 28.76°±0.2°, 29.13°±0.2°, 29.61°±0.2°, 29.97°±0.2°, 30.40°±0.2°, 31.21°±0.2°, 32.26°±0.2°, 32.64°±0.2°, 33.42°±0.2°, 34.66°±0.2°, 35.53°±0.2°, 36.94°±0.2°, 37.57°±0.2°, 38.31°±0.2°, 38.86°±0.2°, 39.21°±0.2°, 40.26°±0.2°, 40.75°±0.2°, 42.56°±0.2°, 43.88°±0.2°, 44.44°±0.2°, 45.09°±0.2°, 45.92°±0.2°, 46.65°±0.2°, 51.44°±0.2°.

4. The salt of claim 1, wherein the methanesulfonate is methanesulfonate crystal form A, and the methanesulfonate crystal form A has an X-ray powder diffraction pattern substantially as shown in FIG. 1.

5. The salt of claim 1, wherein the methanesulfonate is methanesulfonate crystal form A, and the differential scanning calorimeter diagram of the methanesulfonate crystal form A comprises an endothermic peak at 239.57° C.±3° C.

Figure 7:
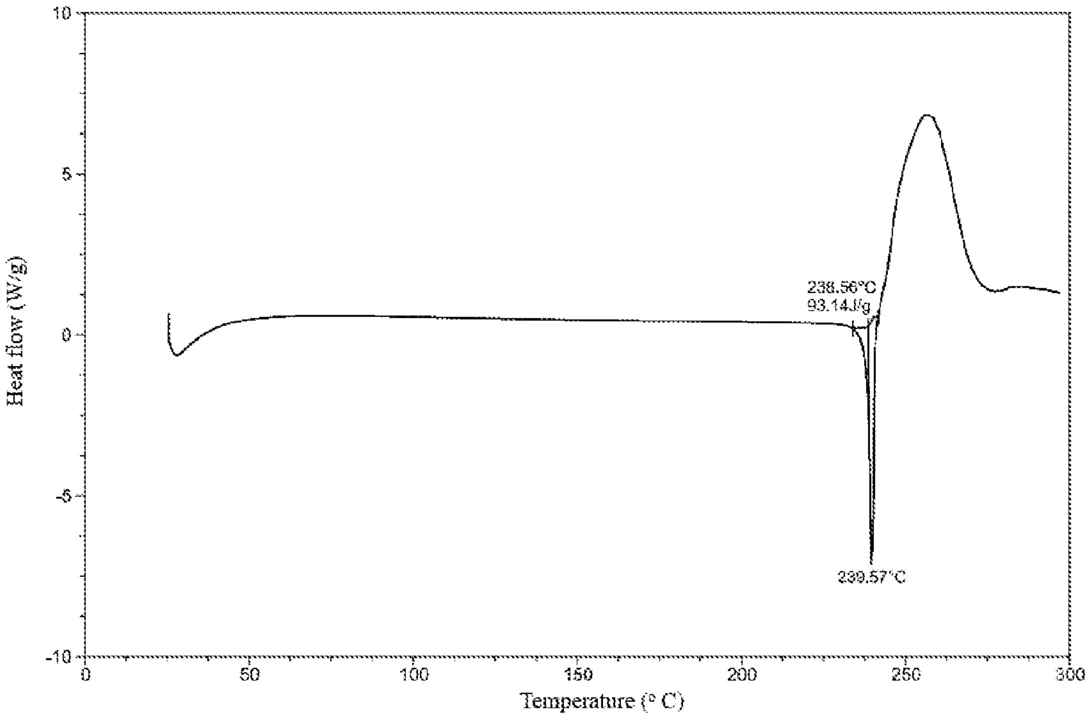
FIG. 7 is a differential scanning calorimetry (DSC) diagram of the methanesulfonate crystal form A of the compound having formula (I).
Figure 8:
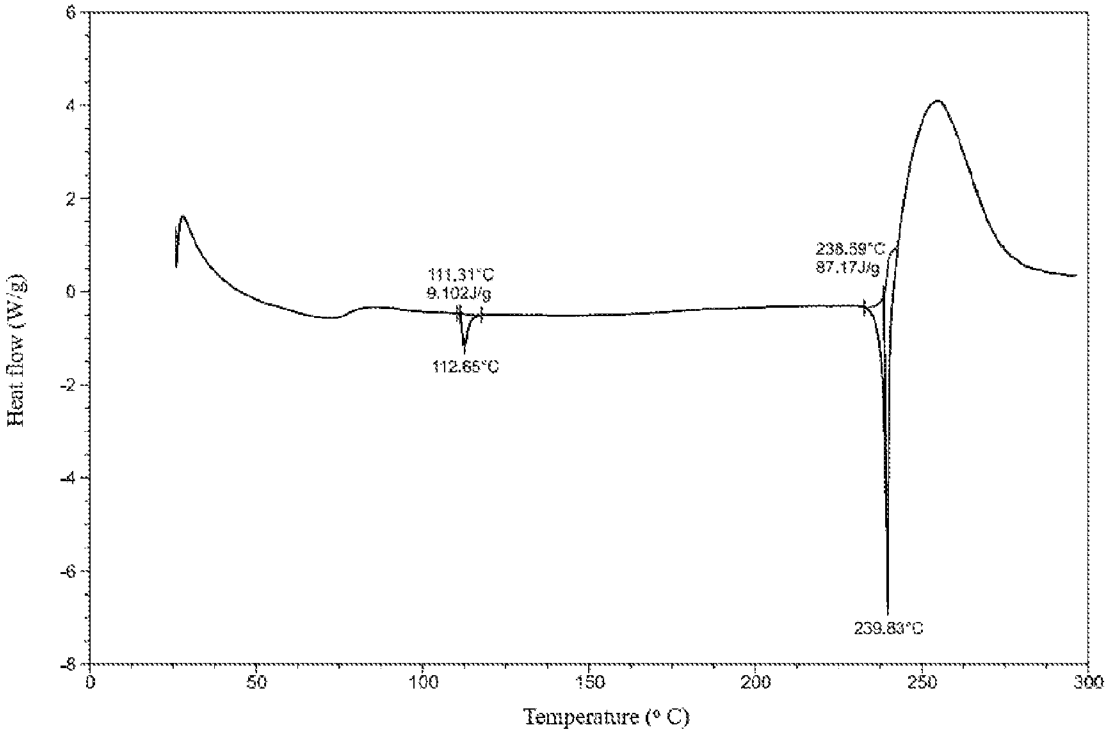
FIG. 8 is a differential scanning calorimetry (DSC) diagram of the methanesulfonate crystal form B of the compound having formula (I).
Figure 9:
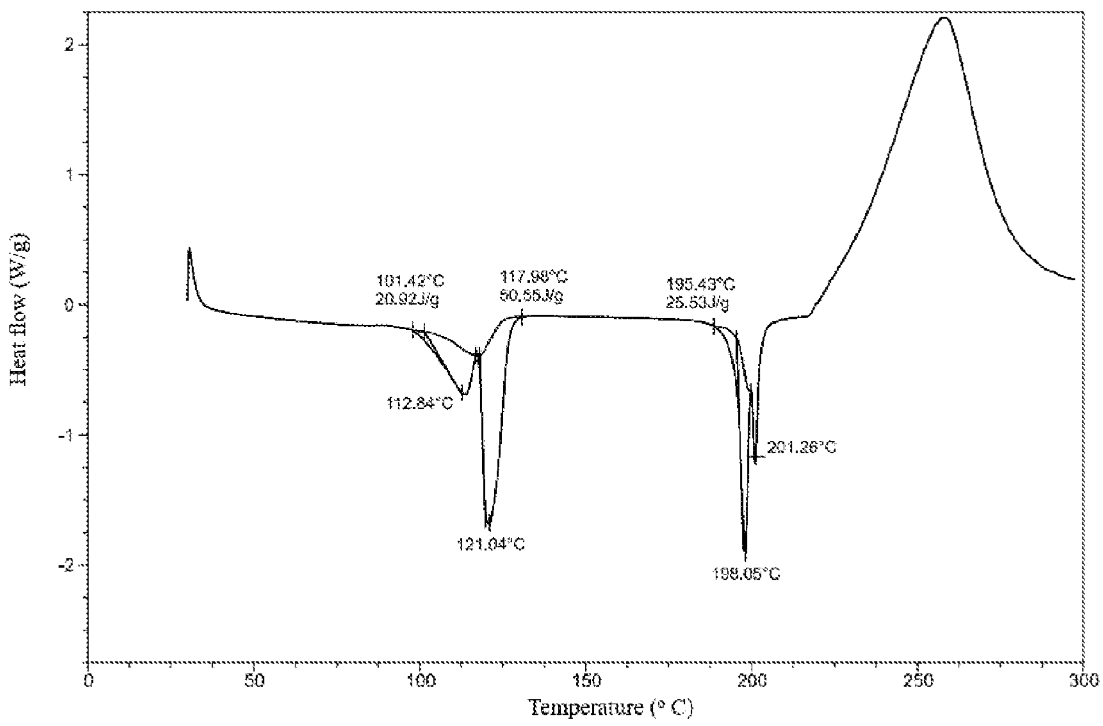
FIG. 9 is a differential scanning calorimetry (DSC) diagram of the benzenesulfonate crystal form A of the compound having formula (I).
Figure 10:
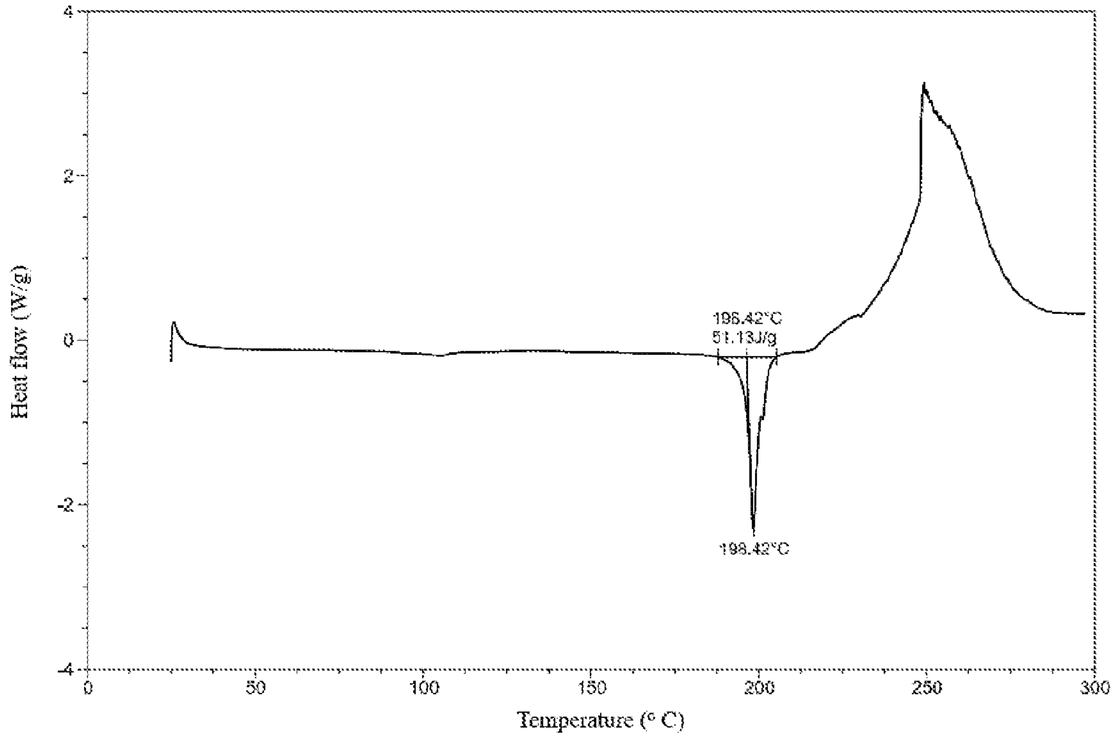
FIG. 10 is a differential scanning calorimetry (DSC) diagram of the benzenesulfonate crystal form B of the compound having formula (I).
Figure 11:
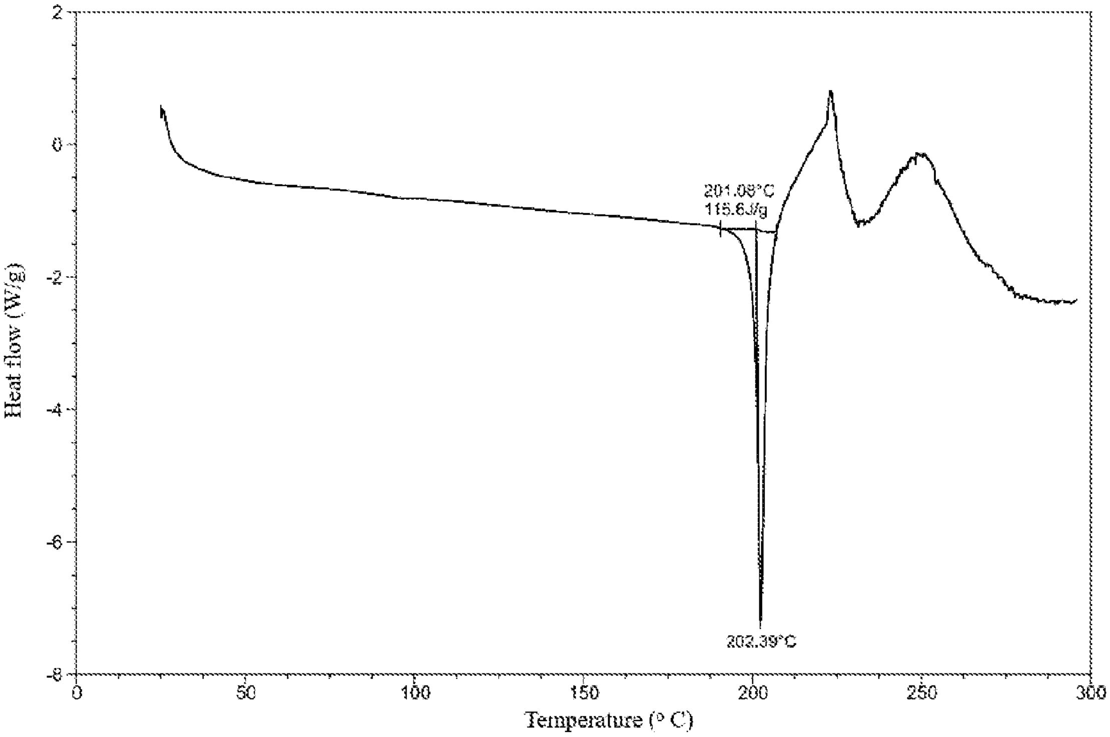
FIG. 11 is a differential scanning calorimetry (DSC) diagram of the fumarate crystal form A of the compound having formula (I).
Figure 12:
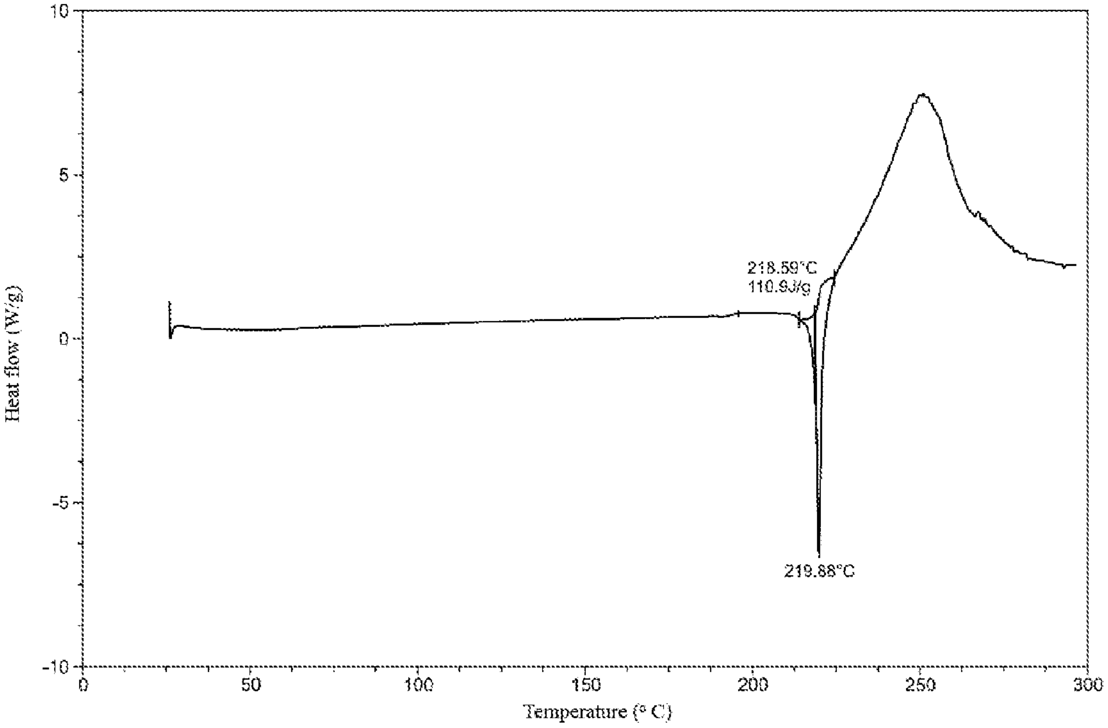
FIG. 12 is a differential scanning calorimetry (DSC) diagram of the fumarate crystal form B of the compound having formula (I).
Figure 13:
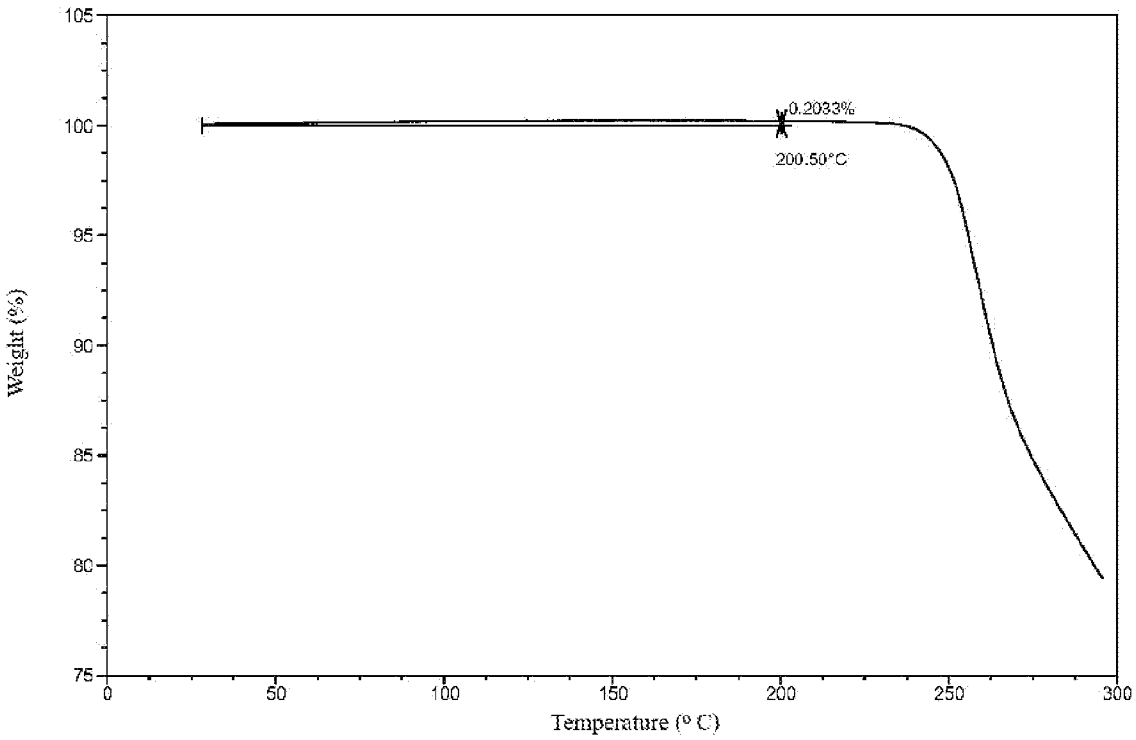
FIG. 13 is a thermogravimetric analysis (TGA) diagram of the methanesulfonate crystal form A of the compound having formula (I).
Figure 14:
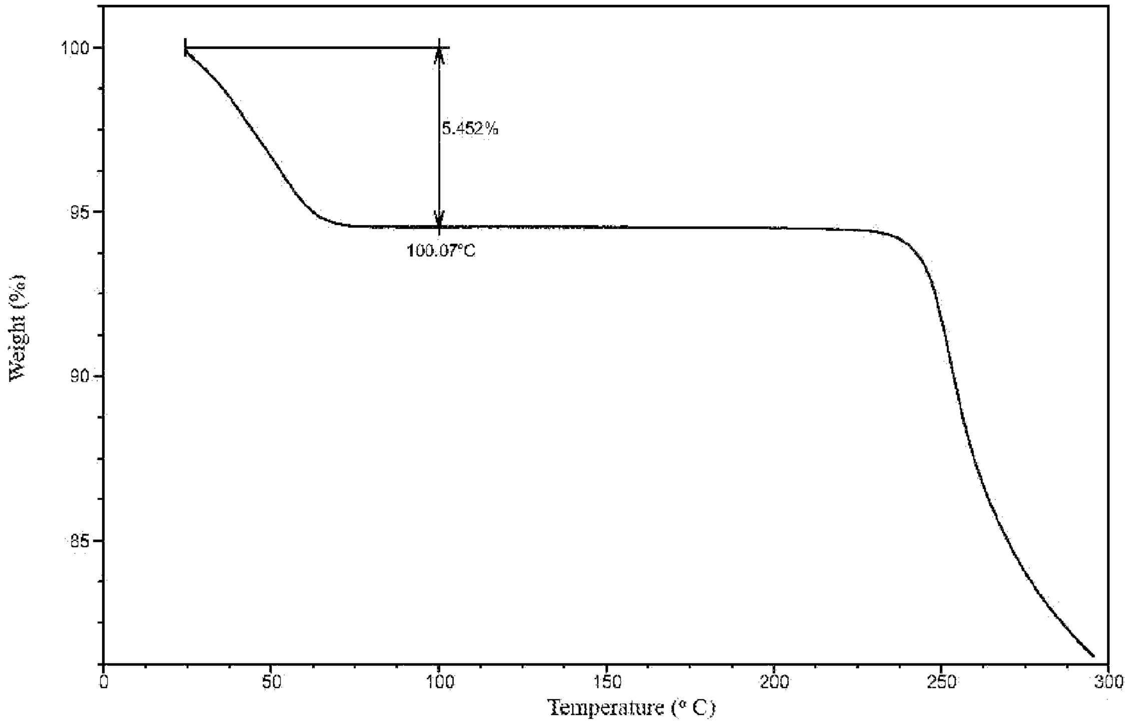
FIG. 14 is a thermogravimetric analysis (TGA) diagram of the methanesulfonate crystal form B of the compound having formula (I).

6. The salt of claim 1, wherein the methanesulfonate is methanesulfonate crystal form A, and the methanesulfonate crystal form A has a differential scanning calorimeter diagram substantially as shown in FIG. 7.

7. A pharmaceutical composition comprising the salt of claim 1, and a pharmaceutically acceptable carrier, excipient, diluent, adjuvant or a combination thereof.

8. A method of preventing treating or lessening a disease in a subject comprising administering to the subject a therapeutically effective amount of the salt of claim 1, wherein the disease is migraine, general pain, trigeminal neuralgia, toothache or temporomandibular joint dysfunction pain, autism, obsessive-compulsive disorder, panic disorder, depression, social phobia, anxiety, generalized anxiety disorder, sleep disorder, post-traumatic syndrome, chronic fatigue syndrome, premenstrual syndrome or post-luteal syndrome, borderline personality disorder, disruptive behavior disorder, impulse control disorder, attention deficit hyperactivity disorder, alcoholism, tobacco abuse, mutism, trichotillomania, excessive appetite, anorexia nervosa, premature ejaculation, erectile dysfunction, memory loss or dementia.

9. A method of preventing, treating, or lessening a disease in a subject comprising administering to the subject a therapeutically effective amount of the composition of claim 7, wherein the diseases is migraine, general pain, trigeminal neuralgia, toothache or temporomandibular joint dysfunction pain, autism, obsessive-compulsive disorder, panic disorder, depression, social phobia, anxiety, generalized anxiety disorder, sleep disorder, post-traumatic syndrome, chronic fatigue syndrome, premenstrual syndrome or post-luteal syndrome, borderline personality disorder, disruptive behavior disorder, impulse control disorder, attention deficit hyperactivity disorder, alcoholism, tobacco abuse, mutism, trichotillomania, excessive appetite, anorexia nervosa, premature ejaculation, erectile dysfunction, memory loss or dementia.

* * * * *